US006775402B2

(12) United States Patent
Bacus et al.

(10) Patent No.: US 6,775,402 B2
(45) Date of Patent: *Aug. 10, 2004

(54) METHOD AND APPARATUS FOR CREATING A VIRTUAL MICROSCOPE SLIDE

(75) Inventors: James W. Bacus, Oakbrook, IL (US); James V. Bacus, Downers Grove, IL (US)

(73) Assignee: Bacus Laboratories, Inc., Lombard, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/365,548
(22) Filed: Feb. 12, 2003
(65) Prior Publication Data

US 2003/0123717 A1 Jul. 3, 2003

Related U.S. Application Data

(63) Continuation of application No. 09/574,423, filed on May 20, 2000, now Pat. No. 6,522,774, which is a continuation of application No. 09/032,514, filed on Feb. 27, 1998, now Pat. No. 6,272,235, which is a continuation-in-part of application No. 08/805,856, filed on Mar. 3, 1997, now Pat. No. 6,101,265.

(51) Int. Cl.$^7$ .................................................. G06K 9/00
(52) U.S. Cl. ...................... 382/133; 382/134; 382/172; 382/305; 707/102; 707/104.1
(58) Field of Search ................................ 382/133, 128, 382/154, 172, 257, 283, 284, 134, 305; 600/407; 707/102, 104.1

(56) References Cited

U.S. PATENT DOCUMENTS 3,999,047 A   12/1976   Green (List continued on next page.)

FOREIGN PATENT DOCUMENTS

EP        0 209 422        1/1987

(List continued on next page.)

OTHER PUBLICATIONS

"The CAS 200™ Multiscan™ Automated Pathology Workstation" by James V. Bacus, Compendium on the Computerized Cytology and Histology Laboratory, Tutorials of Cytology ©1994.

(List continued on next page.)

*Primary Examiner*—Charles Rones
*Assistant Examiner*—Jacques Veillard
(74) *Attorney, Agent, or Firm*—Fitch, Even, Tabin & Flannery

(57) ABSTRACT

A method and apparatus are disclosed for constructing a virtual microscope slide comprised of digitally scanned images from a microscope specimen. The digitally scanned images are arranged in a tiled format convenient for viewing without a microscope, and for transferring the tiled images for viewing by another at a remote location. Several original microscope views at a low magnification are digitized and stored as digitized images coherently seamed together to provide an overall virtual, macro image of the specimen at a lower resolution. Several original microscope views at higher magnifications are digitized and stored as digitized images coherently seamed together to provide virtual micro images at higher resolution. A data structure is formed with these virtual macro and micro digitized images along with their mapping coordinates. Preferably, a generic viewing program is also provided in the data structure that allows remote users to manipulate and interpret the tiled images on the user's monitor. Also, the data structure is formed with significantly compressed data so as to be transmitted over low bandwidth channels, such as the Internet, without loss of resolution that would interfere with the analysis at a remotely-located pathologist receiving the data structure over the Internet. The preferred interactive program allows the pathologist to scroll and view neighboring image areas of interest. A marker on the macro image indicates to the user the location of the micro image and assists the user in selecting areas from the macro image to be viewed at higher resolution and magnification.

23 Claims, 18 Drawing Sheets

U.S. PATENT DOCUMENTS

| | | |
|---|---|---|
| 4,150,360 A | 4/1979 | Kopp et al. |
| 4,175,860 A | 11/1979 | Bacus |
| 4,199,748 A | 4/1980 | Bacus |
| 4,213,036 A | 7/1980 | Kopp et al. |
| 4,523,278 A | 6/1985 | Reinhardt et al. |
| 4,742,558 A | 5/1988 | Ishibashi et al. |
| 4,760,385 A | 7/1988 | Jansson |
| 4,777,525 A | 10/1988 | Preston, Jr. |
| 4,887,892 A | 12/1989 | Bacus |
| 4,965,725 A | 10/1990 | Rutenberg |
| 5,018,209 A | 5/1991 | Bacus |
| 5,068,906 A | 11/1991 | Kosaka |
| 5,072,382 A | 12/1991 | Kamentsky |
| 5,073,857 A | 12/1991 | Peters et al. |
| 5,099,521 A | 3/1992 | Kosaka |
| 5,107,422 A | 4/1992 | Kamentsky et al. |
| 5,123,056 A | 6/1992 | Wilson |
| 5,163,095 A | 11/1992 | Kosaka |
| 5,216,500 A | 6/1993 | Krummey et al. |
| 5,216,596 A | 6/1993 | Weinstein |
| 5,218,645 A | 6/1993 | Bacus |
| 5,252,487 A | 10/1993 | Bacus et al. |
| 5,257,182 A | 10/1993 | Luck et al. |
| 5,260,871 A | 11/1993 | Goldberg |
| 5,268,966 A | 12/1993 | Kasdan |
| 5,287,272 A | 2/1994 | Rutenberg et al. |
| 5,297,034 A | 3/1994 | Weinstein |
| 5,313,532 A | 5/1994 | Harvey et al. |
| 5,333,207 A | 7/1994 | Rutenberg |
| 5,428,690 A | 6/1995 | Bacus et al. |
| 5,473,706 A | 12/1995 | Bacus et al. |
| 5,499,097 A | 3/1996 | Ortyn et al. |
| 5,505,946 A | 4/1996 | Kennedy et al. |
| 5,544,650 A | 8/1996 | Boon et al. |
| 5,625,765 A | 4/1997 | Ellenby et al. |
| 5,655,029 A | 8/1997 | Rutenberg |
| 5,687,251 A | 11/1997 | Erler et al. |
| 5,784,162 A | 7/1998 | Cabib et al. |
| 5,793,969 A | 8/1998 | Kamentsky et al. |
| 5,796,861 A | 8/1998 | Vogt et al. |
| 5,836,877 A | 11/1998 | Zavislan |
| 5,838,837 A | 11/1998 | Hirosawa et al. |
| 5,978,804 A | 11/1999 | Dietzman |
| 5,993,001 A | 11/1999 | Bursell et al. |
| 6,078,681 A | 6/2000 | Silver |
| 6,091,842 A | 7/2000 | Domanik et al. |
| 6,091,930 A | 7/2000 | Mortimer et al. |
| 6,148,096 A | 11/2000 | Pressman et al. |
| 6,151,405 A | 11/2000 | Douglass et al. |
| 6,438,200 B1 * | 8/2002 | Kita .......................... 378/44 |
| 6,469,797 B2 * | 10/2002 | Sakai ....................... 358/1.15 |
| 6,606,413 B1 * | 8/2003 | Zeineh ..................... 382/232 |

FOREIGN PATENT DOCUMENTS

| | | |
|---|---|---|
| EP | 0 246 010 A | 11/1987 |
| JP | 05-313071 | 11/1993 |
| JP | 06-118307 | 4/1994 |
| JP | 07-015721 | 1/1995 |

OTHER PUBLICATIONS

Szeliski R: "Image Mosaicing for Tele–Reality Applications" Proceedings of the IEEE Workshop on Applications of Computer Vision, XX, XX, May 1, 1994, pp. 44–53, XP 002048809.

Szeliski, et al.; "Direct Methods for Visual Scene Recognition" Digital Equipment Corporation, Cambridge Research Lab, pp. 26–33, Jun. 24, 1995.

Krishnan A. et al.; "Panoramic Image Acquisition" Proceedings 1996 IEEE Computer Society Conference on Computer Vision and Pattern Recognition (CAT No. 96CB35909), Proceedings of IEEE Conference on Computer Vision and Pattern Recognition, San Francisco, CA USA Jun. 18–20, 1996.

Dani, et al.; "Automated Assembling of Images: Image Montage Preparation" Department of Electrical Engineering, Indian Institute of Technology, pp. 431–445, Oct. 24, 1993.

"Biomarkers of Premalignant Breast Disease and Their Use as Surrogate Endpoints in Clinical Trails of Chemopreventive Agents" *The Breast Journal*, vol. 1, No. 4, pp. 228–235 (1995), Charges W. Boone and Gary J. Kelloff, 8 pages.

"Markovian Analysis of Cervical Cell Images" *The Journal of Histochemistry and Cytochemistry*, vol. 24, No. 1, pp. 138–144 (1976), Normal J. Pressman, 7 pages.

* cited by examiner

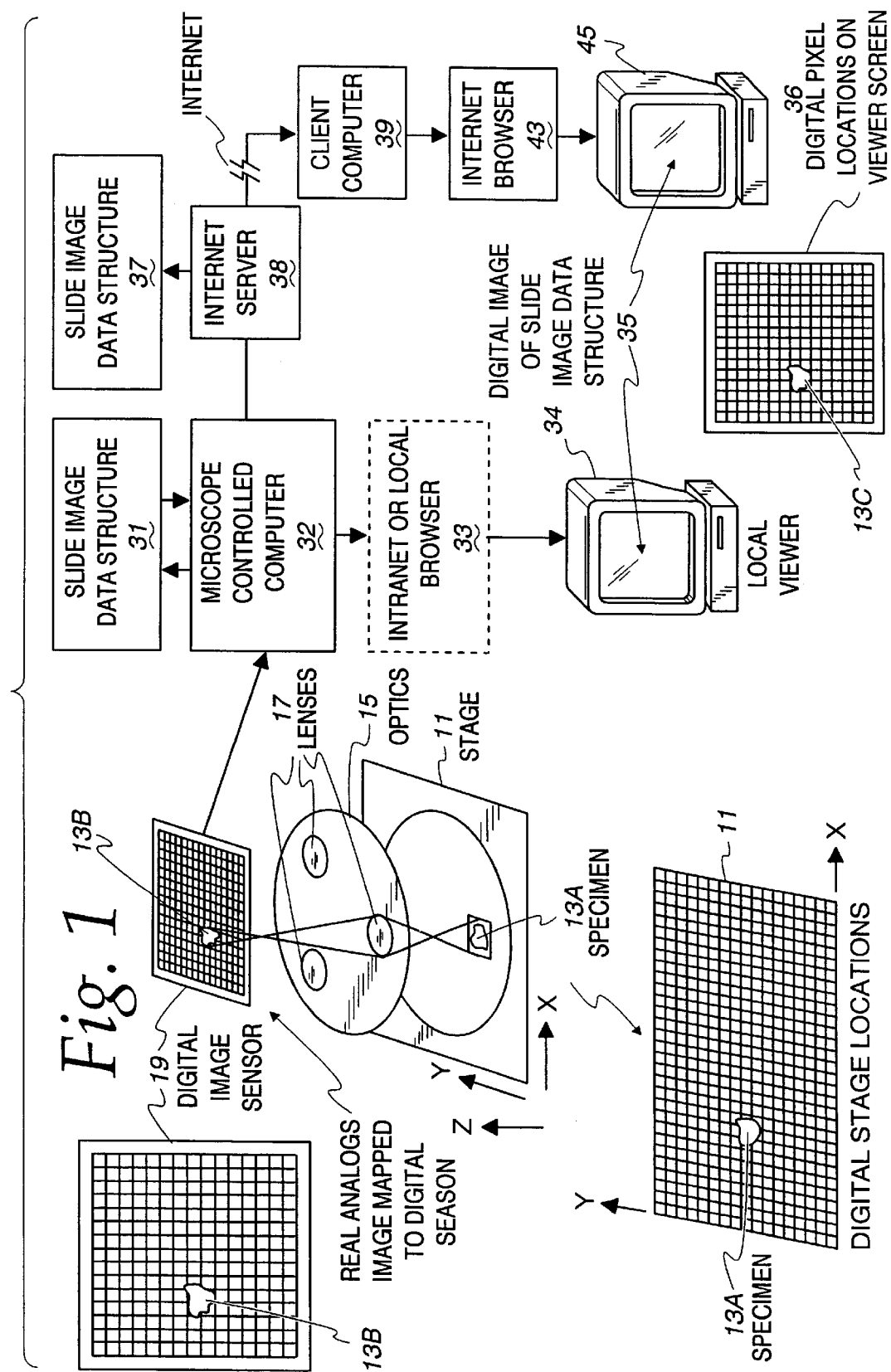

Fig. 7a

Uncompressed Data Files in BMP format

Contents of 'Dcis_027'

| | | | | |
|---|---|---|---|---|
| FinalScan.ini | Da29.bmp | Da55.bmp | Da81.bmp | Ss18.bmp |
| SlideScan.ini | Da3.bmp | Da56.bmp | Da82.bmp | Ss19.bmp |
| Da0.bmp | Da30.bmp | Da57.bmp | Da83.bmp | Ss2.bmp |
| Da1.bmp | Da31.bmp | Da58.bmp | Da84.bmp | Ss20.bmp |
| Da10.bmp | Da32.bmp | Da59.bmp | Da85.bmp | Ss21.bmp |
| Da100.bmp | Da33.bmp | Da6.bmp | Da86.bmp | Ss22.bmp |
| Da101.bmp | Da34.bmp | Da60.bmp | Da87.bmp | Ss23.bmp |
| Da102.bmp | Da35.bmp | Da61.bmp | Da88.bmp | Ss24.bmp |
| Da103.bmp | Da36.bmp | Da62.bmp | Da89.bmp | Ss25.bmp |
| Da104.bmp | Da37.bmp | Da63.bmp | Da9.bmp | Ss26.bmp |
| Da11.bmp | Da38.bmp | Da64.bmp | Da90.bmp | Ss27.bmp |
| Da12.bmp | Da39.bmp | Da65.bmp | Da91.bmp | Ss28.bmp |
| Da13.bmp | Da4.bmp | Da66.bmp | Da92.bmp | Ss29.bmp |
| Da14.bmp | Da40.bmp | Da67.bmp | Da93.bmp | Ss3.bmp |
| Da15.bmp | Da41.bmp | Da68.bmp | Da94.bmp | Ss30.bmp |
| Da16.bmp | Da42.bmp | Da69.bmp | Da95.bmp | Ss31.bmp |
| Da17.bmp | Da43.bmp | Da7.bmp | Da96.bmp | Ss32.bmp |
| Da18.bmp | Da44.bmp | Da70.bmp | Da97.bmp | Ss33.bmp |
| Da19.bmp | Da45.bmp | Da71.bmp | Da98.bmp | Ss34.bmp |
| Da2.bmp | Da46.bmp | Da72.bmp | Da99.bmp | Ss35.bmp |
| Da20.bmp | Da47.bmp | Da73.bmp | Ss1.bmp | Ss36.bmp |
| Da21.bmp | Da48.bmp | Da74.bmp | Ss10.bmp | Ss37.bmp |
| Da22.bmp | Da49.bmp | Da75.bmp | Ss11.bmp | Ss4.bmp |
| Da23.bmp | Da5.bmp | Da76.bmp | Ss12.bmp | Ss5.bmp |
| Da24.bmp | Da50.bmp | Da77.bmp | Ss13.bmp | Ss6.bmp |
| Da25.bmp | Da51.bmp | Da78.bmp | Ss14.bmp | Ss7.bmp |
| Da26.bmp | Da52.bmp | Da79.bmp | Ss15.bmp | Ss8.bmp |
| Da27.bmp | Da53.bmp | Da8.bmp | Ss16.bmp | Ss9.bmp |
| Da28.bmp | Da54.bmp | Da80.bmp | Ss17.bmp | mda027.TRA |

Fig. 7b

BliFinalScanFrame.class
BliMessageBox.class
BliWebSlide.class

Fig. 8

Index.HTML for file 'Dcis_027'

Contents of 'Dcis_027'

| | | | | |
|---|---|---|---|---|
| WebSlide | Da29.jpg | Da55.jpg | Da81.jpg | Ss18.jpg |
| index.html | Da3.jpg | Da56.jpg | Da82.jpg | Ss19.jpg |
| Da0.jpg | Da30.jpg | Da57.jpg | Da83.jpg | Ss2.jpg |
| Da1.jpg | Da31.jpg | Da58.jpg | Da84.jpg | Ss20.jpg |
| Da10.jpg | Da32.jpg | Da59.jpg | Da85.jpg | Ss21.jpg |
| Da100.jpg | Da33.jpg | Da6.jpg | Da86.jpg | Ss22.jpg |
| Da101.jpg | Da34.jpg | Da60.jpg | Da87.jpg | Ss23.jpg |
| Da102.jpg | Da35.jpg | Da61.jpg | Da88.jpg | Ss24.jpg |
| Da103.jpg | Da36.jpg | Da62.jpg | Da89.jpg | Ss25.jpg |
| Da104.jpg | Da37.jpg | Da63.jpg | Da9.jpg | Ss26.jpg |
| Da11.jpg | Da38.jpg | Da64.jpg | Da90.jpg | Ss27.jpg |
| Da12.jpg | Da39.jpg | Da65.jpg | Da91.jpg | Ss28.jpg |
| Da13.jpg | Da4.jpg | Da66.jpg | Da92.jpg | Ss29.jpg |
| Da14.jpg | Da40.jpg | Da67.jpg | Da93.jpg | Ss3.jpg |
| Da15.jpg | Da41.jpg | Da68.jpg | Da94.jpg | Ss30.jpg |
| Da16.jpg | Da42.jpg | Da69.jpg | Da95.jpg | Ss31.jpg |
| Da17.jpg | Da43.jpg | Da7.jpg | Da96.jpg | Ss32.jpg |
| Da18.jpg | Da44.jpg | Da70.jpg | Da97.jpg | Ss33.jpg |
| Da19.jpg | Da45.jpg | Da71.jpg | Da98.jpg | Ss34.jpg |
| Da2.jpg | Da46.jpg | Da72.jpg | Da99.jpg | Ss35.jpg |
| Da20.jpg | Da47.jpg | Da73.jpg | Ss1.jpg | Ss36.jpg |
| Da21.jpg | Da48.jpg | Da74.jpg | Ss10.jpg | Ss37.jpg |
| Da22.jpg | Da49.jpg | Da75.jpg | Ss11.jpg | Ss4.jpg |
| Da23.jpg | Da5.jpg | Da76.jpg | Ss12.jpg | Ss5.jpg |
| Da24.jpg | Da50.jpg | Da77.jpg | Ss13.jpg | Ss6.jpg |
| Da25.jpg | Da51.jpg | Da78.jpg | Ss14.jpg | Ss7.jpg |
| Da26.jpg | Da52.jpg | Da79.jpg | Ss15.jpg | Ss8.jpg |
| Da27.jpg | Da53.jpg | Da8.jpg | Ss16.jpg | Ss9.jpg |
| Da28.jpg | Da54.jpg | Da80.jpg | Ss17.jpg | |

*Fig. 9A*
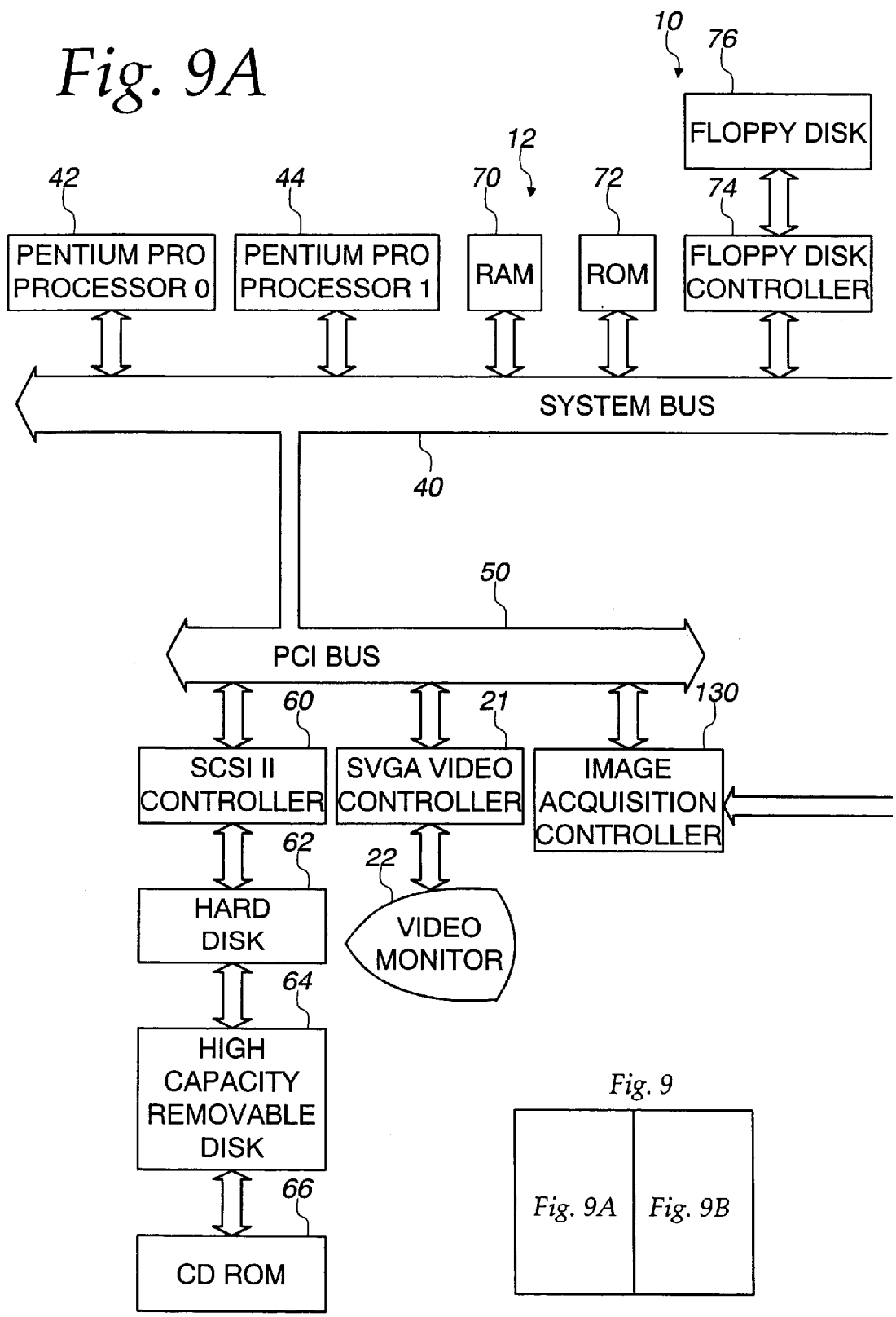
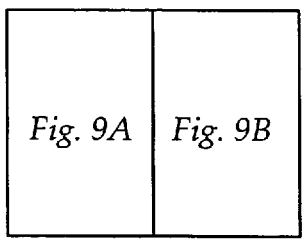

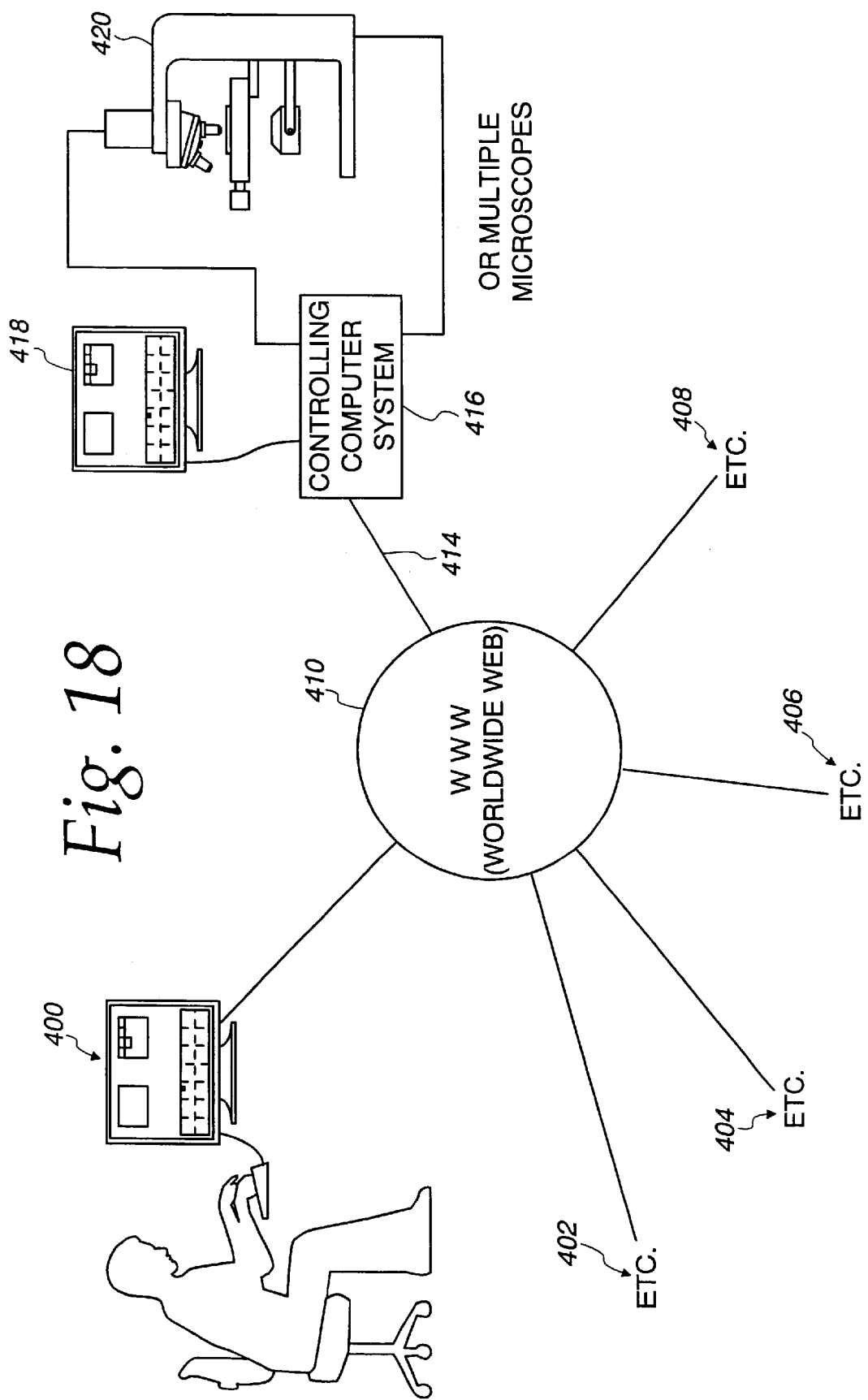

METHOD AND APPARATUS FOR CREATING A VIRTUAL MICROSCOPE SLIDE

This patent application is a continuation patent application of patent application Ser. No. 09/574,423, filed on May 20, 2000, now U.S. Pat. No. 6,522,774, which is a continuation of patent application No. 09/032,514, filed on Feb. 27, 1998, now U.S. Pat. No. 6,272,235, which is a continuation-in-part of patent application Ser. No. 08/805,856, filed on Mar. 3, 1997, now U.S. Pat. No. 6,101,265.

FIELD OF THE INVENTION

Which is a Continuation patent application of U.S. patent application Ser. No. 09/032,514, filed Feb. 27, 1998, now U.S. Pat. No. 6,272,235, which is a Continuation-in-Part of prior U.S. patent application Ser. No. 08/805,856, Filed Mar. 3, 1997, now U.S. Pat. No. 6,101,265, which is hereby incorporated by reference in its entirety.

BACKGROUND OF THE INVENTION

The invention described in the aforesaid application answers a need, a requirement to image and digitally record an object in a relatively flat plane at high resolution/magnification. Today, it is impractical to construct an optical image sensor large enough to cover the entire image area e.g., of a specimen on a microscope slide, at the required resolution. This is because lens size and resolution/magnification issues limit the size of the field of view of magnified objects and their resulting images. Viewing through a microscope is akin to viewing through a periscope in that one sees a very small field of view even at low magnifications, such as 1.25×. A pathologist using a microscope often scans a slide to obtain in his mind an overall view or sense of what constitutes the specimen and he remembers the general locations of the diagnostically significant, small pieces of the specimen. Usually, these are the diseased areas, such as malignant or potentially malignant portions of the specimen. To obtain higher resolution and magnification of these suspicious portions, the pathologist switches to a higher magnification objective lens but then the field of view becomes much smaller again. Often, the pathologist switches back and forth between the lower magnification, larger field of view objective lens to orient himself relative to the specimen and the high magnification, smaller field of view to obtain the detailed, high resolution view of the suspicious area on the specimen. Thus, the user never receives a magnified, condensed overall view of the specimen or a portion of the specimen but must remember the series of views taken at low magnification. Likewise, at high resolution, high magnification, the user never receives or views a collection of adjacent images but must interrelate these successive images in the user's mind.

A similar problem exists on the Internet or intranet where a pathologist may receive a single field of view magnified image taken from a specimen over the Internet or the intranet on his browser. The pathologist must be provided with explanations to coordinate the high resolution view with the lower resolution view. The number of views available to the pathologist is very limited, and the pathologist is unable to select other views or to scroll to neighboring views at the areas that are most interesting to the pathologist.

In the aforesaid prior application, there is disclosed a method and apparatus whereby a person may construct a low magnification, digitized overall, image view of the entire specimen on a slide or a selected portion of the specimen on a slide, such as the basal layer of a tissue section. The overall, low magnification digitized image allows the user to understand where the user is presently located in his viewing and where the user may want to make the next observation. That is, the low magnification overall view is generally in color and provides to the experienced user a visual overall or thumbnail view of the slide and shows the possible areas of interest for malignancy or other diseases which manifest themselves at certain locations on the specimen image being viewed. This low magnification overall view enables the user to select thereon the points of interest that the user wants to view at a higher magnification.

The overall view was constructed by taking by a large number of low magnification images of the specimen through a microscopic scanning system and then coherently assembling and coordinating these respective smaller views or images (hereinafter "image tiles") into one coherent, low magnification, macro image from the specimen. Often the digitized macro image is reduced in size by a software system to even a smaller size to be displayed on a local screen or to be transferred over a low bandwidth or a high bandwidth channel to a remote viewing screen.

The prior application teaches how to assemble a large number of image tiles, for example, 35 image tiles for the macro image, and then to take a series of other tiles of a higher magnification or magnifications which will also be viewed by the user. To this end, the user is provided with a marker, such as a cursor or the like, to select the defined area of interest, and by a simple command, to cause the selected, higher magnification digitized images to appear on the screen for viewing by the user. The higher magnification images may be one of several magnifications or resolutions such as 10×, 20× and 40×.

As disclosed in the aforesaid application, it is preferred to allow the user, such as a pathologist, to quickly flip back and forth between the high resolution micro image and the low macro resolution image or to provide separate split screens whereby the pathologist is shown an overall macro view and a marker showing where the current higher magnification view is located. Because of the multiple magnifications, the user may change to an intermediate magnification such as would be accomplished by switching between intermediate objective lenses. This provides the pathologist with views which correspond to changing back and forth between objective lenses in a microscope, a procedure with which most pathologists are familiar and have been trained.

Additionally, the aforesaid application provides the user with a scrolling feature that allows the user to shift into the viewing screen adjacent, magnified images on the screen so that the pathologist is not limited to only seeing just a full tile view but may see adjacent image material from adjacent, neighboring tile images.

In the aforesaid patent application, there is a disclosure of transmitting the low magnification image over a local area network or over the Internet through various servers and computers. The tiled images that were being transmitted were achieved by use of a fully computer controlled microscope which allowed the user to navigate along a specimen area of interest, such as along a basal area or to other suspicious points spread throughout the specimen to acquire tiled images of selected areas so that the entire specimen would not have to be digitized and stored. As disclosed in the preferred embodiment in the aforesaid application, an Internet browser remotely-controlled, automated microscope could be used by a pathologist from a remote location to view the reconstructed macro image tiles; and, with his manipulation of the microscope, using an intranet or Internet browser, could acquire single images at higher magnifications if desired. While several people could see the particular digitized images being transmitted out over the Internet as they were acquired by a particular pathologist and several people could view the stored images, there was still a problem of control at operation of the microscope by each person viewing the digitized images, and a problem with acquiring and transmitting large areas of higher magnification images using the tiling method.

As stated above in greater detail, the current state of archiving the digital images achieved through a microscope is often by having photographs or by video tapes. The photographs are difficult to use as is a video tape particularly when the user wants to move rapidly back and forth between various images and to scroll through various adjacent parts of the specimen image. Further, current archival methods lack an overall macro image of the specimen, which allows the user to know exactly where the particular high resolution view is from when it is making an analysis of the high resolution image.

While digitized images can be stored magnetically or otherwise digitized and recorded on various recording mediums, no current archival system allows the user to toggle back and forth between high magnification images and low magnification images or between various images at different magnifications such as that achieved by a pathologist switching microscope objective lenses in real time to get the macro and micro images from the same location on the specimen. Heretofore, the practice of pathology has been relatively limited to the use of microscopes and to the pathologist having to use the microscope to review the particular specimen.

There is a need for a dynamic system whereby one or more or several pathologists, including a consulting pathologist, may view the same area simultaneously and interact with one another either in diagnosis or in analysis. Also, it would be best if the images from the specimen could be stored so that a pathologist could easily examine the images at his leisure using an intranet or Internet browser at a later date merely by accessing the particular web site where the images are located.

It will be appreciated that a host of problems need to be solved to allow Internet or intranet users to view on their respective monitors useful, low resolution, macro images and high resolution, micro images of several adjacent, original microscope images. One of the first problems is how to seam together neighboring tile images to form a seamless overall view of these tiles. Heretofore, attempts to seam the tiles used software to combine the pixels at the tile boundaries and have been generally unsuccessful. Another problem is that of mapping of coordinates beginning with the coordinates, usually X and Y coordinates, from and at the microscope stage carrying the slide and then the mapping of coordinates on the scanning screen not only for one magnification but also to coordinate the mapping for the respective multiple resolution images taken typically at 1.25×, 10× and 40× or more. These coordinates must be maintained for a large number of tiled images, e.g., 40 tiled images for one macro image. In order for the remote user to view these tile images and to flip back and forth between different resolution, tiled images, the user's computer and monitor not only must receive the addresses and stored parameters for each pixel but must also run them on a generic viewing program.

Another problem with acquiring image tiles and sending them over a low bandwidth Internet channel is that both the storage requirements on the server and the amount of data acquired per slide become high, such as for example, 120 megabytes to one gigabyte. The 120 megabytes is only achieved by not taking image tiles of the entire specimen but only image tiles from the areas selected by the pathologist when tracing at high resolution along basal layers or only at the dispersed, suspicious cancer appearing area in a breast cancer. Even with this selective interaction by a pathologist in constructing the macro and micro digitized images with a vastly reduced amount of image tiles relative to that which would be acquired if the entire specimen where imaged at each of the multiple magnifications, the acquired amount of data is a monstrous problem of transmitting in a reasonable amount of time over a narrow bandwidth channel to an ordinary web browser having limited storage capacity. While rough compression techniques could be used, they cannot be used at the expense of providing the high resolution image that the pathologist must have for diagnosis of the specimen.

SUMMARY OF THE INVENTION

In accordance with the present invention, there is provided a new and improved method and apparatus for constructing digitally scanned images from a microscope specimen, for storing the digitally scanned images in a tiled format convenient for viewing without a microscope, and for transferring the tiled images at multiple magnifications for viewing by another at a remote location. This is achieved by assembling together several adjacent, original microscope views at a first magnification to obtain an overall macro view of the specimen and assembling together several adjacent original microscope views at a higher magnification to create a combined data structure. The data structure may then be transferred to the remote viewer to provide this viewer multiple resolution macro and micro images of areas on the slide specimen. The data structure is constructed by digitally scanning and storing the low magnification images with their mapping coordinates and likewise, digitally scanning and storing higher magnification images with their mapping coordinates. Further, a pathologist may interactively select only those diagnostically significant areas of the specimen for digital scanning and storing to reduce significantly the number of image pixels stored at high resolution.

The data structure can be transmitted over the Internet or intranet to allow multiple users to consult on a particular microscope each using his own virtual images of the specimen. These users each may flip back and forth between different resolution images in a manner similar to that achieved when shifting among objective lens for different resolution views. However, the preferred embodiment of this invention provides a marker on the overall macro view showing the remote user where the higher resolution image is located on the specimen so that the user does not have to remember the location of the higher resolution image. Unlike the single, small optical field of view currently available, the remote user is provided with a series of abutted, tiled images each being substantially equal to one small optical field of view. Thus, the remote user is provided with better and larger macro and micro tiled images than the single, small optical fields of view taken at the same magnifications of a single tiled image.

The preferred data structure is also provided with a generic viewing program that allows the remote user to manipulate and interpret the tiled images on the user's browser. This generic viewing program is self-contained with its own display and the interpretative program is usable with a variety of computers, browsers and monitors. The data structure uses selectively compressed data to reduce the huge amount of acquired data, e.g. 120 megabytes, into a small amount of data, e.g. 1.4 megabytes. Such smaller, more manageable amounts of data can be transmitted over a low bandwidth channel such as the Internet without the loss of resolution that would interfere with the remote pathologist's analysis. Further, the interactive program allows the pathologist to scroll and to view neighboring image areas of neighboring image tiles which were currently unavailable to the pathologist until the inventions set forth in the aforesaid application and in this application.

Turning now in greater detail to aspects of this invention, problems with achieving tileable (i.e. contiguous images which can be seamlessly abutted next to each other to recreate the original image, but at different magnifications) multiple images of a specimen on a microscope slide are overcome by the system of the invention. The system includes a microscope and stage in which digital locations on the stage have been predetermined in accordance with an electromechanical addressable coordinate system (X-Y for convenience). Each point on the stage is assigned an "X" and a "Y" coordinate which uniquely defines its location. The increments in each of the X and Y directions are established at a predefined amount for example in 0.1 micrometer increments. A key factor in achieving superior resolution of the specimen images at higher magnifications is to establish many more physical increments on the stage for each pixel of the image sensor and of the intended display. For example, at 1.25× magnification, 64 points on the stage correspond to one pixel on a CCD optical sensor, which corresponds to one pixel on a 640 by 480 monitor (for a VGA display), using the bitmap addressing and scrollable image method described herein.

Once the coordinate system is defined for the microscope stage, when a specimen on a microscope slide is placed on it, each feature of interest on the slide can be uniquely located with reference to the stage. Then the microscope system is used to digitally scan the image. The first scan is done at a relatively small magnification since this image will be used to provide a "macro" image of the entire specimen. In the preferred embodiment, 1.25× magnification is used. The microscope system then scans the slide using the 1.25× objective. Since the image is detected by rectangular optical sensors, such as the optical sensors in a CCD grid, the stage must be moved in relatively larger increments to place the next adjacent physical part of the slide exactly in the region where that rectangular area will be precisely imaged on the CCD sensor.

Although the area traveled is relatively large, the precision must be high to enable alignment of the image parts within the pixel resolution of the CCD sensor. For example, at the 1.25× magnification, 48,143 X steps and 35,800 Y steps are necessary to move the specimen object on the stage to a new, contiguous region for optical imaging on the CCD sensor. The signal produced by the optical sensors in the CCD grid are then transmitted to a computer which stores the image signals in a series of tiled images. Since each image frame is defined by predetermined X-Y coordinates, these can be easily converted into a series of contiguous tiled images.

To view the scanned digital image on a monitor, the computer uses a method of reserving an image bitmap corresponding to the entire size of the tiled image, e.g., in this instance, 10×8, 1.25× magnified tiled images are acquired. This requires an image bitmap of 7,520×3,840 in size, using a 752×480 pixel CCD sensor. Since the X-Y coordinates are known for each image tile, and thus for each pixel in each tile, the bitmap can be used to coordinate and display the stored image tiles to present a fused macro view of the image with one-to-one pixel correspondence of the screen pixels with the image pixels. Typically, the screen pixels are fewer in X-Y size than the macro tiled image, (that is, the entire image cannot be viewed on the monitor without some sort of image compression); and in this case, the macro tiled image is scrolled on the viewable window segment of the screen to maintain the one-to-one correspondence. An advantage of the one-to-one correspondence is that significant image detail is available to the user. Further, since the physical X,Y position on the specimen is known through the stage coordinate relationship to the image pixels, the tiled macro images can be used to locate regions, and move the stage to that region from collection of higher magnification tiled images.

Since the nature of optics, i.e. lenses, is that they provide a generally circular image with a sharp central region and with fuzziness around the periphery of the image, the microscope system is designed to step through the various locations on the slide in such a manner to scan only the high resolution image portion in the center of the optical image. The fuzzy outer regions are discarded. This also has the benefit of ensuring a high resolution image once the tiled images are reconstructed for viewing by a user on a monitor.

After the macro image is completed, a trained professional, such as an examining pathologist, views the image of the specimen by viewing the macro image and looking for areas of interest. In general, most specimen slides contain only a few small areas of diagnostic significance. The balance of the slide is generally empty or not significant. When the examining pathologist views the slide, some areas may have been previously marked in the regions of interest for viewing and analysis at higher magnifications. Once these regions are marked, the microscope is set to the desired higher magnification and then only the marked regions are scanned and stored. Alternatively, he may define new areas directly on the macro image. In either case, the regions are outlined using a pointing device, such as a mouse, directly on the viewing window displaying the macro image. As described above with respect to the 1.25× images, since the stage has a predefined coordinate system, the scanned higher magnification image portions can be easily located with respect to the macro image, creating a series of micro images.

The fact that a typical microscope specimen slide contains only limited information of interest and the ability of the system embodying the invention to accurately locate such regions enables the system to create a virtual microscope slide, i.e. a data structure which can be used in place of the actual specimen slides. This advantageously enables multiple users to consult on a particular specimen. Additionally, because of the reduced size of the data structures, they can be viewed locally on a personal computer, transmitted over an intranet or via the Internet globally. The created data structures can be stored on a variety of storage or recording media: for example, on a server's hard disk, a Jazz drive, a CD-Rom or the like. Storing the data structure on a portable storage media further enables the transfer and archiving of the microscopic slide data structures by multiple users.

Another feature of the invention is a self-executing data structure. This is achieved by packaging the tiled images with an active, dynamic control program. When an active dynamic control program is used by a viewing program such as a common web browser, the browser can interpret the dynamic control program. This allows the user to interact and control the viewed images seen on the viewer's screen from the recording medium. More specifically, in the preferred embodiment of the invention, a large number of low magnification, digitized tiled images are formed and embedded in a data structure with linking information allowing them to be coherently tiled to each other during viewing to form a macro image, and a series of higher magnification tiled images also similarly constructed into a micro image, and a control program such as a JAVA applet, is provided and transferred with the macro and micro tiled images for use by a remote user. Thus, for example, the macro and micro tiled images with their active control program may be transmitted over an Internet or an intranet to a browser, or other application program for viewing the images, where the user may then access the browser to analyze the images at multiple resolutions and with a macro field of view before the user. This enables the viewing of the images in a manner similar to the use of an optical microscope, but in this case visually the view is of a virtual microscope slide at multiple resolutions.

Also, in accordance with the invention, the constructed, tiled macro and tiled micro images along with the control program can be placed on a web server and can be accessed locally and over a wide area, even globally, by multiple users at various times. For instance, a large number of previously scanned and recorded specimen slides, such as 300 specimen slides, may have their respective micro and macro tiled images put on a server. Medical students or pathology students then may each access the slide or all of the 300 slides and review them on their respective web browsers at their leisure. Likewise, a pathologist may dial up or otherwise connect through an internet service provider to the Internet or other long-level network and access a web server and obtain a particular patient's specimen results. Those results would have been stored as a data structure (including macro and micro tiled images along with the control and interpretative program). The pathologist then may and perform an analysis at his home or in his office without needing to have or to control a microscope or the particular slide. The pathologist may toggle back and forth between the micro and macro images, and then dictate or otherwise prepare his analysis, findings or diagnosis from these stored images. This advantageously enables the pathologist to perform part of his job in the convenience of his home or office and also enables a laboratory to maintain actual specimen slides in a safe and secure location, away from the potential of damage and without the necessity of shipping the slides for microscopic examination at a remote location.

The control program, which in the preferred embodiment of the invention is a dynamic self-executing program such as a JAVA applet, allows the user to manipulate and interpret the images while on a browser. The dynamic, self-executing program is completely self-contained with its own display and interpretative program for operation by the user of the browser.

The present invention is not limited to use on a browser since the tiled, digitized images and the active, control program may be stored on a CD-ROM or other portable storage medium and sent through the mail, or otherwise transferred to the user for review at the user's convenience with dedicated viewers.

Thus, from the foregoing, it will be seen that there is provided a new and improved method of and apparatus for archiving of microscopic slide information on a storage medium with an active control program, which allows the display and interpretation of various micro and macro images.

In accordance with another important aspect of the invention, there is provided with the self-executing data structure (the stored macro images, micro images and dynamic, self-executing program for viewing, reconstructing and manipulating the stored images) the ability to scroll through the displayed images. This allows the user not only to see one image tile at a particular magnification, but also to use a pointer or to otherwise move a point to cause displayed images from adjacent neighboring image tiles which were not previously viewable to be included in the field being viewed by the user. That is, the user may shift the viewing location across tile boundaries from one tile to another, and up or down, or right or left or to other points of interest in a normal two-dimensional scrolling manner. Thus, the user is provided with an archived stored slide at multiple magnifications which can be readily scrolled through in any arbitrarily chosen direction or directions. As in the aforesaid application, the user interactively will go to various areas of selected interest and operate a pointer or a marker to select for high magnification viewing the particular area of interest and also do a scrolling of neighboring areas of interest.

In addition to the Internet browser, the data images can be viewed, reconstructed and manipulated using a dynamic, self-executing program such as, for example, a JAVA applet or an ACTIVE-X applet. An advantage of using a dynamic, self-executing program which is linked with the data images on a data structure is that the data images can be viewed, reconstructed and manipulated independent of the operating system of the users computer. Additionally, the user does not have to acquire the latest version of the dynamic, self-executing program since it is already linked with and provided with the data images on the data structure or on the storage medium. Thus, the user can always view the data images, regardless of different program versions.

The dynamic, self-executing program permits interchanging the image in its entirety simulating the visual effect of changing objectives in a regular, mechanical optical microscope view. Thus, the user can easily switch from one magnification to another and scroll through portions of the image, simulating tracking the image by moving the slide under the microscope lens.

The dynamic, self-executing program permits scrolling the image in a window to enable viewing of the reconstructed large field of view images. The user can use a mouse, or other pointing device, to select a portion of the image on the large field of view image and the program will display that selected portion in another window at the desired magnification.

A method of constructing a record of the digital image of a specimen on a microscope slide using image tiles includes scanning the image at a first low magnification so that substantially all of the specimen is obtained. Then the specimen is scanned at a second higher magnification so that images of selected (or all) sub-portions of the specimen are obtained. The spatial relationships of the first lower magnification image to the second higher magnification images is used to reconstruct the image during viewing. The individual, sub-portions or tiles of the scanned image are seamed together by the dynamic, self-executing program to create a digital image of substantially larger areas than individually acquired image fields of view without tiling.

A data structure according to the invention is created by first digitally scanning the desired specimen at a plurality of image magnifications. The scanned images are then stored in a series of contiguous image tiles. Then the stored images are linked with a dynamic, self-executing program. The data structure can be created using a software program. Images are preferably first stored as bitmap files (.bmp). (Note that storing the resulting image files in the bitmap format is different from the bit mapping method of creating the image files described herein.) An image compression program is used to convert the bitmap files to a JPEG (.jpg) format, which requires less storage space and consequently less time to display on a computer. The person creating the data structure can select how much detail to include in the conversion. JPEG images can be created for example, using 20 to 80% compression ratios of the original image. An advantage of the JPEG format is that essentially empty tiles (tiles with mostly white or black space) compress down to very small files. Detailed files, however, do not compress as much. Additionally, the dynamic, self-executing program may include compression algorithms for displaying the entire image or portions thereof in the viewing window.

After downloading or installation of a data structure on a storage medium, when the user desires to view the data images, he uses a mouse and "clicks" on the icon for the self-executing data structure. The dynamic, self-executing program displays the image in a window. Typically, the program will display a macro or thumbnail view of the entire specimen image at a lower magnification and a smaller window containing a particular image tile or groups of tiles at a higher magnification. The program enables the user to use the mouse or other pointing device to select a point or outline a region on the thumbnail view. The selected view will then be displayed in the smaller window at the second magnification. The user can move the mouse or pointing device and the image in the smaller window will scroll with the selection on the thumbnail view. In this way, the program simulates movement of a microscope slide under the field of view of the mechanical microscope. However, it should be noted that because of the one-to-one correspondence between the CCD pixels and the screen pixels, not all macro images may be able to be displayed on the monitor. The user may scroll through the macro image or select a compression feature to display the entire macro image in the window.

Another feature of the self-executing data structure is that when the image is displayed on the viewing screen, the user can select an image tile or sub-portion of the image and alternately view that portion of the image at each scanned magnification. For example, if the data was scanned at magnifications of 1.25x, 20x and 40x, the user can "click" and see the same tile at each of those magnifications alternately.

BRIEF DESCRIPTION OF THE DRAWINGS

FIG. 1 is a block diagram of a system according to the invention for creating and transmitting locally, over an intranet or via the Internet data structures of an image of specimen on a microscope slide;

FIG. 7A is a file listing such as would be seen under Windows 95 file manager showing the data files included in a data structure for a breast cancer specimen;

FIG. 7B is a file listing of a Java applet for controlling a data structure;

FIG. 8 is file listing such as would be seen under Windows 95 file manager showing the data files included in an alternate data structure for a breast cancer specimen;

FIGS. 9A and 9B are a block diagram of the apparatus embodying the present invention;

FIG. 18 is a block diagram of a remote networked system for distributing and accessing diagnostic images and data, i.e. virtual microscope slides, through a hypertext transport protocol based server directly or over a packet network.

DETAILED DESCRIPTION OF THE PREFERRED EMBODIMENT

Figure 1A:
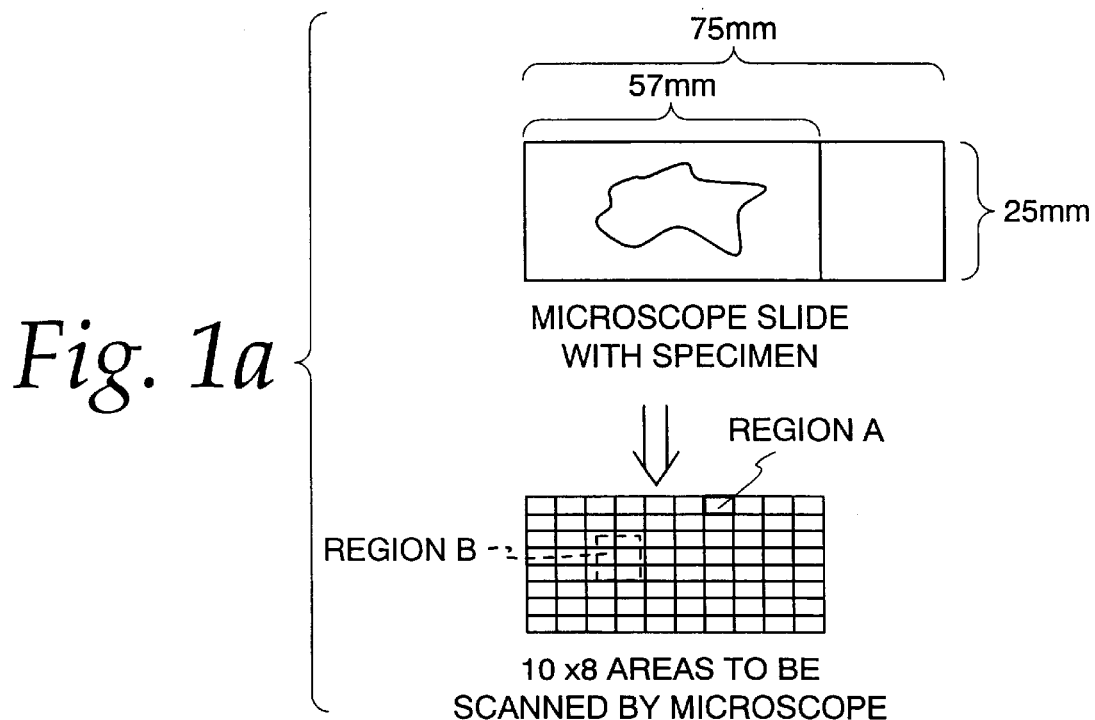
FIG. 1A is representation of a microscope slide which has been arbitrarily assigned to be scanned into eighty tiled images.

FIG. 1 is a block diagram of a system according to the invention for creating, and transmitting over an intranet or via the Internet a virtual microscope slide, i.e. interrelated data structures and display procedures depicting at multiple resolutions, images of a specimen on a microscope slide. The system includes a microscope with a digital platform for supporting the microscope slide. Digital platform or stage 11 has been specially calibrated to include a large number of increments for locating portions of specimen images with high precision. After calibration and initial registration of stage 11 in the microscope setup, a microscope slide or other substrate with a specimen to be scanned is placed on stage 11.

For exemplary purposes, the creation of virtual microscope slide specimen according to the invention will be described with respect to a breast cancer specimen. The first step in creating a data structure according to the invention is to establish a macro image of the entire specimen (or that portion of the specimen desired to be stored as the macro image). The purpose for creating the macro or large area thumbnail image is to enable the viewer to see the entire specimen at once and to use the entire image to choose those significant portions thereof for viewing at greater magnification. In this example, the user has selected 1.25× as the magnification to display the entire breast cancer slide. Once specimen 13a has been placed on stage 11, rotating optical assembly 15 are rotated to select lens 17 which corresponds to the 1.25× magnification.

In accordance with the teachings of the prior patent application, the computer controlled microscope is moved to scan the entire image of specimen 13a. The focusing system is programmed to step through increments which detect/select only the high resolution center area of the field of view in order to avoid storing the fuzzy areas at the periphery of the field of view. In this example, the macro image will be stored in a 10 by 8 array, for a total of 80 contiguous image tiles, as shown in FIG. 1A.

A typical microscope slide is about 77 mm by 25 mm, where the usable area, without including the label, is about 57 mm by 25 m. Each of the 80 image segments is about 4.8 mm by 3.5 mm in dimension. This means each of the 80 image segments will be scanned separately and stored as a separate image tile.

The precision of the microscope systems is set up so that each step of the motor has a precision of 0.1 micron (micrometer). In this example, the microscope is set up to move 48,143 steps in the X direction and 35,800 steps in the Y direction at 1.25× magnification for each of the 80 image areas. At higher magnifications, the image areas to scan are considerably smaller, so the number of steps is correspondingly smaller. For each of the 80 image areas, the microscope lens will detect only the high resolution center area of the field of view.

Figure 1B:
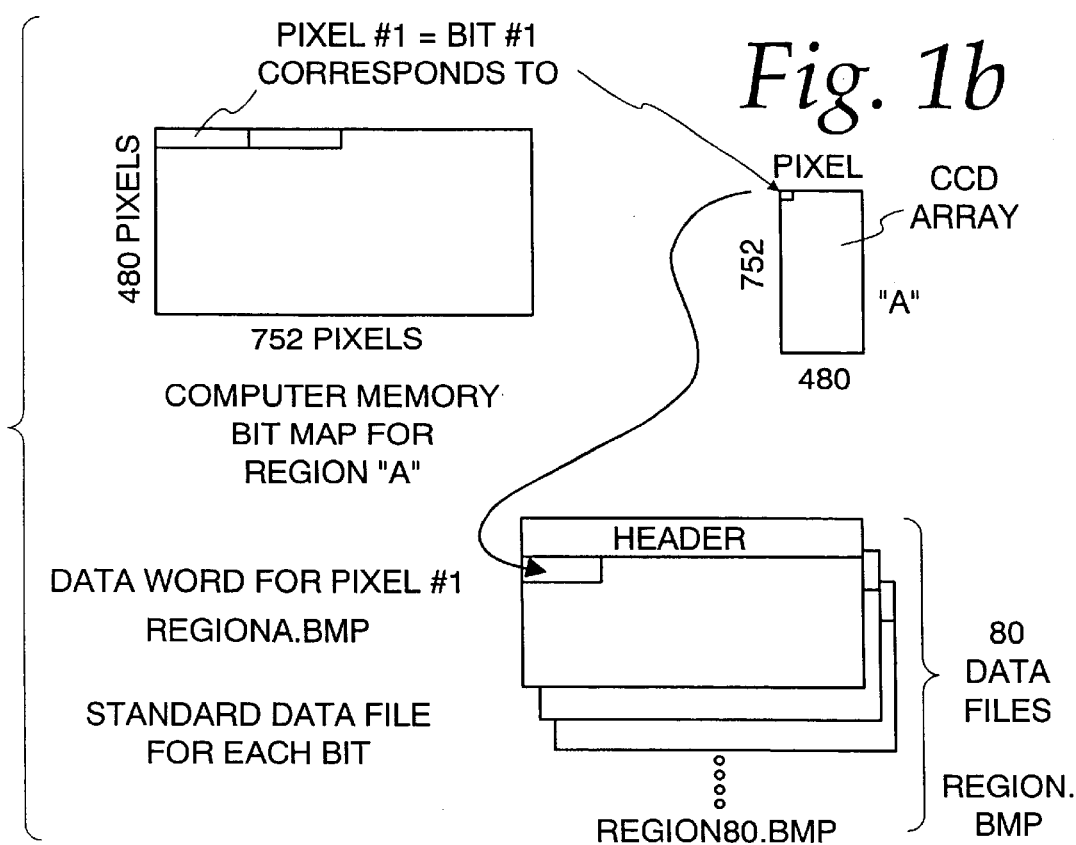
FIG. 1B is a representation of the detected signals of the individual pixel sensors in a CCD optical array after detecting a selected image area to tile and the referenced data files containing the information describing the detected signals.

The optical image of the desired image area is then detected by optical array sensor 19 (preferably a CCD sensor array). In this example, each of the 80 scanned areas is sensed by the entire array, which includes 752 pixels by 480 pixels. The optical array sensor sends electrical signals indicative of the detected image to microscope controlled computer 32. Computer 32 stores the scanned images, including the top left X-Y stage coordinates for each of the 80 individual areas of the microscope slide. Each of the 80 scanned image areas' pixel locations are stored in a bit mapped file (i.e., a file which contains a map of the location of each bit in the area) which corresponds to the layout of the individual images thereon. Thus, all of the pixels from the image tile derived from region A on FIG. 1A, which is the seventh from the left and in the top row, are individually assigned unique locations in the computer memory's bit-mapped file (FIG. 6), and are also stored in the data structure image tile file as shown in FIG. 1B.

Each of the stored data image tiles is a standard image file with extension.bmp, and is of the order of one megabyte, i.e. each of the 752×480 pixels is stored as 3 bytes of red, green and blue image data (752×480×32=1,082,880 bytes). Since the location of each image tile is known according to the bitmap, the complete microscope image can be recreated by painting (displaying) each image tile in accordance with its grid location. It should be noted To display the resulting image, computer 32 calculates the appropriate portion to be displayed from each image tile depending upon the relative-size of the display screen. Since the stored image data is usually greater than the size of the typical monitor, the viewer must scroll through the image on the window to view it entirely. However, an optional compression algorithm can be used to compress the entire image into the viewing window. The X-Y coordinate information is used by the viewing and manipulation program to reconstruct the image tiles into a complete image of the specimen. The resulting image is larger, and with better resolution than would be achieved if optics technology were able to construct a single lens capable of viewing the entire specimen in one field of view. In this example, each of the 80 image tiles has digital resolution of 752×480 pixels, with corresponding optical resolution of approximate 0.2 microns at 40× to approximately 6.4 microns at 1.25×.

After the macro or thumbnail images are digitally scanned and stored with their X-Y coordinate information, the user then examines the macro image or original specimen for significant details. Typically, the user will highlight with a marking pen the areas to be viewed at higher magnification. The user then changes the magnification of optics system 15 to the desired higher magnification, moves the scanning system to bring the selected region into view. Computer 32 then repeats the scanning and image tile creation process for the selected region, but at higher magnification and with a new grid system to locate the scanned selected regions.

In the example, the user has selected region B shown on FIG. 1A to perform a second view at a higher magnification. The user selects, for example, a 40× magnification. The computer calculates the number of tiles to cover the selected area at 40× magnification and sets up a second grid.

It should be noted that region B crosses over several of the larger tiles in FIG. 1A. Because of the extreme precision of the instrument, 0.1 micron resolution, locating such selected regions with high resolution is readily accomplished. As noted above, the compute calculates the size of the image portion, in this case as an example, X=1500 and Y=1200 stepping increments. Each image portion at the 40× resolution is detected by the optical sensor array, 752 by 480 pixels. Each resulting data file is stored in a separate, high magnification mapped area of memory so that the computer can easily recall the location of region B, or any of its 200 individual image tiles, when requested by a user.

Once the user has completed selecting and having the computer controlled microscope system scan and store the digital images in image tiles, computer 32 stores the mapped .bmp files along with their coordinate information and creates slide image data structure 31 in FIG. 1. Slide image data structure includes all of the bitmap image tile files at both magnifications (note that similarly, additional images could be stored at further magnifications, if desired), as well as X-Y coordinate information for the location of the various image tiles.

FIG. 7A is a file listing such as would be seen under a Windows 95 file manager showing the data files included in a data structure for a breast cancer specimen. Included in the file listing are FinalScan.ini and SlideScan.ini as well as sixty bitmap data files. Slidescan.ini is a listing of all the original bitmap (.bmp) files. The bitmap files represent the individual image tiles in the scan at, say, 1.25× magnifications. Slidescan.ini is set forth below in Table 1 and describes the X-Y coordinates for each image tile file. When the data structure is viewed by a control program, the program uses the X-Y coordinates to display all the image tiles contiguously.

TABLE 1

Slidescan.ini

```
[Header]
x = 278000
y = 142500
1XStepSize = 48143
1YStepSize = 35800
iScannedCount = 37
[Ss1]
x = 181714
y = 142500
[Ss2]
x = 133571
y = 142500
[Ss3]
x = 37285
y = 106700
[Ss4]
x = 85428
y = 106700
[Ss5]
x = 133571
y = 106700
[Ss6]
x = 181714
y = 106700
[Ss7]
x = 229857
y = 106700
[Ss8]
x = 229857
y = 70900
[Ss9]
x = 181714
y = 70900
[Ss10]
x = 133571
y = 70900
[Ss11]
x = 85428
y = 70900
[Ss12]
x = 37285
y = 70900
[Ss13]
x = −10858
y = 70900
[Ss14]
x = −10858
y = 35100
[Ss15]
x = 37285
y = 35100
[Ss16]
x = 85428
y = 35100
[Ss17]
x = 133571
y = 35100
[Ss18]
x = 181714
y = 35100
[Ss19]
x = 229857
y = 35100
[Ss20]
x = 278000
y = −700
[Ss21]
x = 229857
y = −700
[Ss22]
x = 181714
y = −700
```

TABLE 1-continued

Slidescan.ini

```
[Ss23]
x = 133571
x = −700
[Ss24]
x = 85428
y = −700
[Ss25]
x = 37285
y = −700
[Ss26]
x = −10858
y = −700
[Ss27]
x = −10858
y = −36500
[Ss28]
x = 37285
y = −36500
[Ss29]
x = 85428
y = −36500
[Ss30]
x = 133571
Y = −36500
[Ss31]
x = 181714
y = −36500
[Ss32]
x = 229857
y = −36500
[Ss33]
x = 278000
y = −36500
[Ss34]
x = 278000
y = −72300
[Ss35]
x = 229857
y = −72300
[Ss36]
x = 181714
y = −72300
[Ss37]
x = 133571
y = −72300
```

Table 2 is a listing of the file FinalScan.ini, which is a listing the X-Y coordinates of the high magnification image tiles scanned and stored.

TABLE 2

FinalScan.ini

```
[Header]
tPatientID = mda027
tAccession =
tOperatorID = jwb
tTimeOfScan = 8/4/97 1:19:56 PM
1XStageRef = 278000
1YStageRef = 142500
iImageWidth = 752
iImageHeight = 480
1XStepSize = 1590
1YStepSize = 1190
1XOffset = −1900
1YOffset = −400
dMagnification = 40
1AnalysisImageCount = 105
1CalibrationImageCount = 0
[Da0]
x = 214532
y = 65584
```

TABLE 2-continued

FinalScan.ini

[Da1]
x = 212996
y = 65584
[Da2]
x = 211460
y = 65584
[Da3]
x = 209924
y = 65584
[Da4]
x = 208388
y = 65584
[Da5]
x = 206852
y = 65584
[Da6]
x = 205316
y = 65584
[Da7]
x = 203780
y = 65584
[Da8]
x = 214532
y = 64400
[Da9]
x = 212996
y = 64400
[Da10]
x = 211460
y = 64400
[Da11]
x = 209924
y = 64400
[Da12]
x = 208388
y = 64400
[Da13]
x = 206852
y = 64400
[Da14]
x = 205316
y = 64400
[Da15]
x = 203780
y = 64400
[Da16]
x = 214532
y = 63216
[Da17]
x = 212996
y = 63216
[Da18]
x = 211460
y = 63216
[Da19]
x = 209924
y = 63216
[Da20]
x = 208388
y = 63216
[Da21]
x = 206852
y = 63216
[Da22]
x = 205316
y = 63216
[Da23]
x = 203780
y = 63216
[Da24]
x = 214532
y = 62032
[Da25]
x = 212996
y = 62032

TABLE 2-continued

FinalScan.ini

[Da26]
x = 211460
y = 62032
[Da27]
x = 209924
y = 62032
[Da28]
x = 208388
y = 62032
[Da29]
x = 206852
y = 62032
[Da30]
x = 205316
y = 62032
[Da31]
x = 203780
y = 62032
[Da32]
x = 214532
y = 60848
[Da33]
x = 212996
y = 60848
[Da34]
x = 211460
y = 60848
[Da35]
x = 209924
y = 60848
[Da36]
x = 208388
y = 60848
[Da37]
x = 206852
y = 60848
[Da38]
x = 205316
y = 60848
[Da39]
x = 203780
y = 60848
[Da40]
x = 214532
y = 59664
[Da41]
x = 212996
y = 59664
[Da42]
x = 211460
y = 59664
[Da43]
x = 209924
y = 59664
[Da44]
x = 208388
y = 59664
[Da45]
x = 206852
y = 59664
[Da46]
x = 205316
y = 59664
[Da47]
x = 203780
y = 59664
[Da48]
x = 214532
y = 58480
[Da49]
x = 212996
y = 58480
[Da50]
x = 211460
y = 58480

TABLE 2-continued

FinalScan.ini

[Da51]
x = 209924
y = 58480
[Da52]
x = 208388
y = 58480
[Da53]
x = 206852
y = 58480
[Da54]
x = 205316
y = 58480
[Da55]
x = 203780
y = 58480
[Da56]
x = 180740
y = 82160
[Da57]
x = 179204
y = 82160
[Da58]
x = 177668
y = 82160
[Da59]
x = 176132
y = 82160
[Da60]
x = 174596
y = 82160
[Da61]
x = 173060
y = 82160
[Da62]
x = 171524
y = 82160
[Da63]
x = 180740
y = 80976
[Da64]
x = 179204
y = 80976
[Da65]
x = 177668
y = 80976
[Da66]
x = 176132
y = 80976
[Da67]
x = 174596
y = 80976
[Da68]
x = 173060
y = 80976
[Da69]
x = 171524
y = 80976
[Da70]
x = 180740
y = 79792
[Da71]
x = 179204
y = 79792
[Da72]
x = 177668
y = 79792
[Da73]
x = 176132
y = 79792
[Da74]
x = 174596
y = 79792
[Da75]
x = 173060
y = 79792

TABLE 2-continued

FinalScan.ini

[Da76]
x = 171524
y = 79792
[Da77]
x = 180740
y = 78608
[Da78]
x = 179204
y = 78608
[Da79]
x = 177668
y = 78608
[Da80]
x = 176132
y = 78608
[Da81]
x = 174596
y = 78608
[Da82]
x = 173060
y = 78608
[Da83]
x = 171524
y = 78608
[Da84]
x = 180740
y = 77424
[Da85]
x = 179204
y = 77424
[Da86]
x = 177668
y = 77424
[Da87]
x = 176132
y = 77424
[Da88]
x = 174596
y = 77424
[Da89]
x = 173060
y = 77424
[Da90]
x = 171524
y = 77424
[Da91]
x = 180740
y = 76240
[Da92]
x = 179204
y = 76240
[Da93]
x = 177668
y = 76240
[Da94]
x = 176132
y = 76240
[Da95]
x = 174596
y = 76240
[Da96]
x = 173060
y = 76240
[Da97]
x = 171524
y = 76240
[Da98]
x = 180740
y = 75056
[Da99]
x = 179204
y = 75056
[Da100]
x = 177668
y = 75056

TABLE 2-continued

FinalScan.ini

[Da101]
x = 176132
y = 75056
[Da102]
x = 174596
y = 75056
[Da103]
x = 173060
y = 75056
[Da104]
x = 171524
y = 75056

Computer 32 can also use the scanned image files to create a self-executing data structure. By compressing the .bmp images to .jpg and adding a dynamic, self-executing program which enables the user to view, reconstruct and manipulate the image tiles, the user can use the data structure as a virtual microscope slide of the original specimen. Preferably, the dynamic, self-executing program is a Java applet, such as shown on FIG. 7B.

Computer 32 can provide the slide image data structure 31 directly or via an intranet browser 33 to local viewer 34, or via an Internet server 38. Slide image data structure 37 is shown as being directly accessible from Internet server 38. Alternatively, a user can download the slide image data structure on his own computer 39, use an internet browser 43 and view the reconstructed images. Another alternative is for computer 32 to store the slide image data structure on a CD-rom, Jazz drive or other storage medium.

To view slide image data structure 31 or 37, the user, who for example, has acquired the data structure via a CD-rom, first installs the CD-rom in the CD-rom drive of his computer. Then the user opens up a browser or other applications program which can read the Java applet installed on the CD-rom with the image tiles. Note that in some instances no separate browser program may be required. In some case, the CD-rom may include the complete applications program for viewing, reconstructing and manipulating the image tiles. In the instant example, the user will then select the icon or file listing for the slide image data structure and the control program will display the data files.

Figure 2:
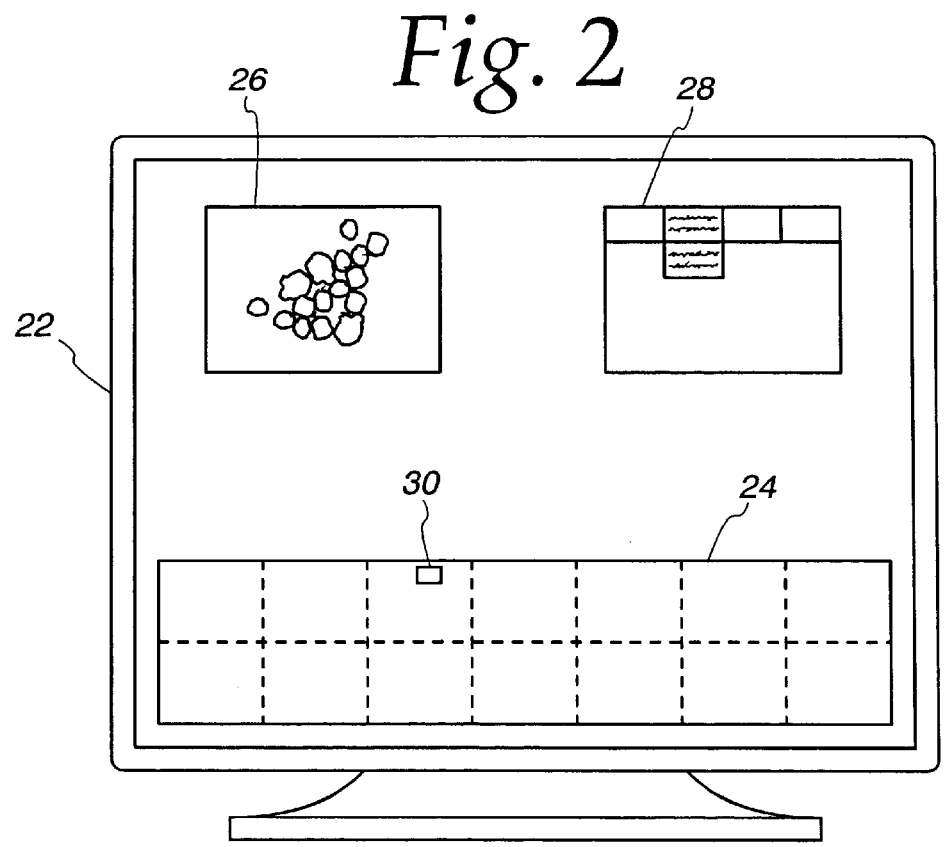
FIG. 2 is a screen view of a system embodying the present invention showing a low magnification image of a specimen on a microscope slide in one window, a high magnification image of a portion of the low magnification image selected by a region marker and a control window.
Figure 3:
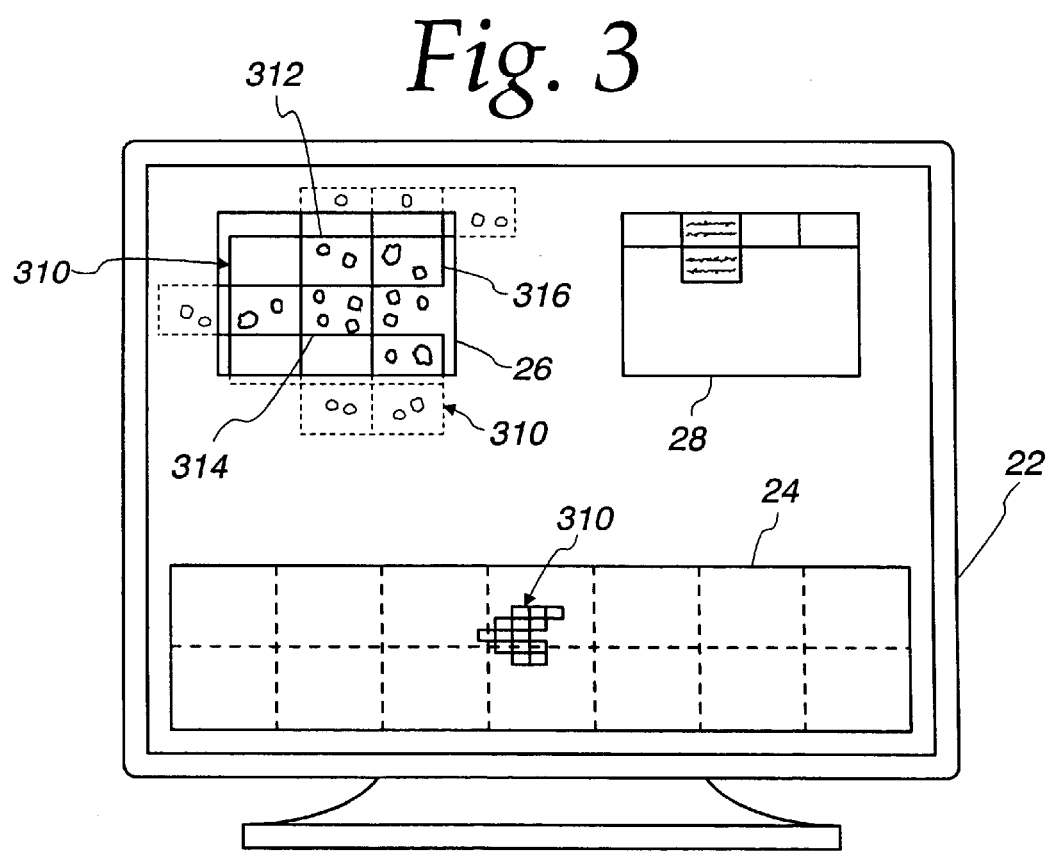
FIG. 3 is a view of a display screen of the apparatus embodying the present invention showing the control window a low magnification window having a plurality of high magnification micro image regions delineated therein and a high magnification window including one or more of the micro image regions.
Figure 4:
FIG. 4 is a view of a macro image of an actual breast cancer specimen displayed at 1.25x as seen on a computer monitor.
Figure 5:
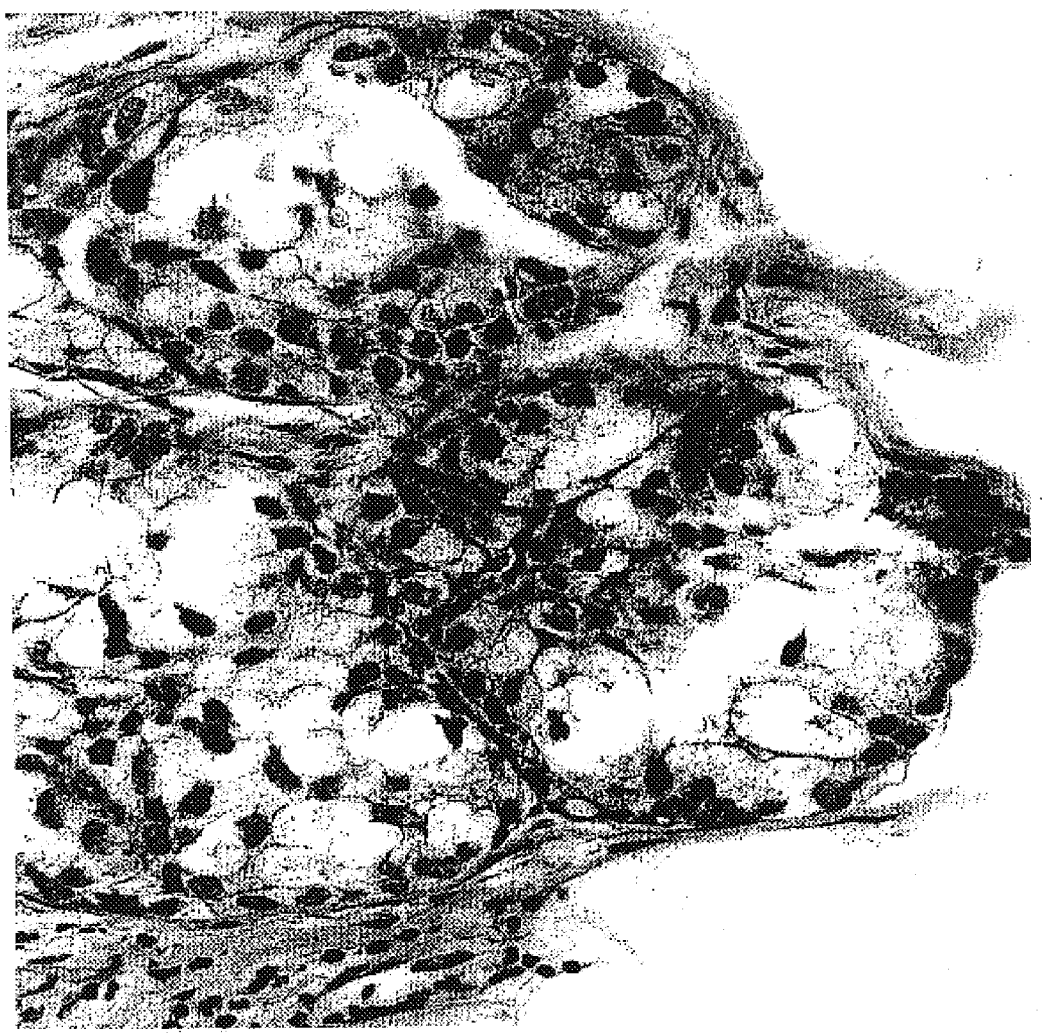
FIG. 5 is a view of the grid portion of FIG. 4 outlining a region of interest selected by a pathologist displayed at 40x magnification.

FIG. 2 is a screen view of a system embodying the present invention showing a low magnification image 24 of a specimen on a microscope slide in one window, a high magnification image 26 of a portion of the low magnification image selected by a region marker 30 and a control window 28. FIG. 3 is a view of a display screen of the apparatus embodying the present invention showing the control window 28, a low magnification window 24 having a plurality of high magnification micro image regions 310 delineated therein and a high magnification window 26 including one or more of the micro image regions 310, 314, 316. FIG. 4 is a view of a macro image of an actual breast cancer specimen displayed at 1.25× as seen on a computer monitor. FIG. 5 is a view of the grid portion of FIG. 4 outlining a region of interest selected by a pathologist displayed at 40× magnification.

Recall that region A in FIG. 1A was about 4.8 mm by 3.5 mm. This area creates 752 by 480 pixels of sensed data, or 360,930 pixels of information. Each pixel sends information about its location and the image it sensed to the computer. The computer stores this information in a series of data files (typically .bmp format, but .tif or .gif could also be used). Thus, it can be seen that several more pixels of sensed data are available for viewing on a computer monitor operating at 640 by 480. To view the entire image, the user must scroll through the image tiles. However, scrolling need not be done on a tile, by tile basis. Rather, the user scrolls by pointing to a pixel on the monitor.

Figure 6:
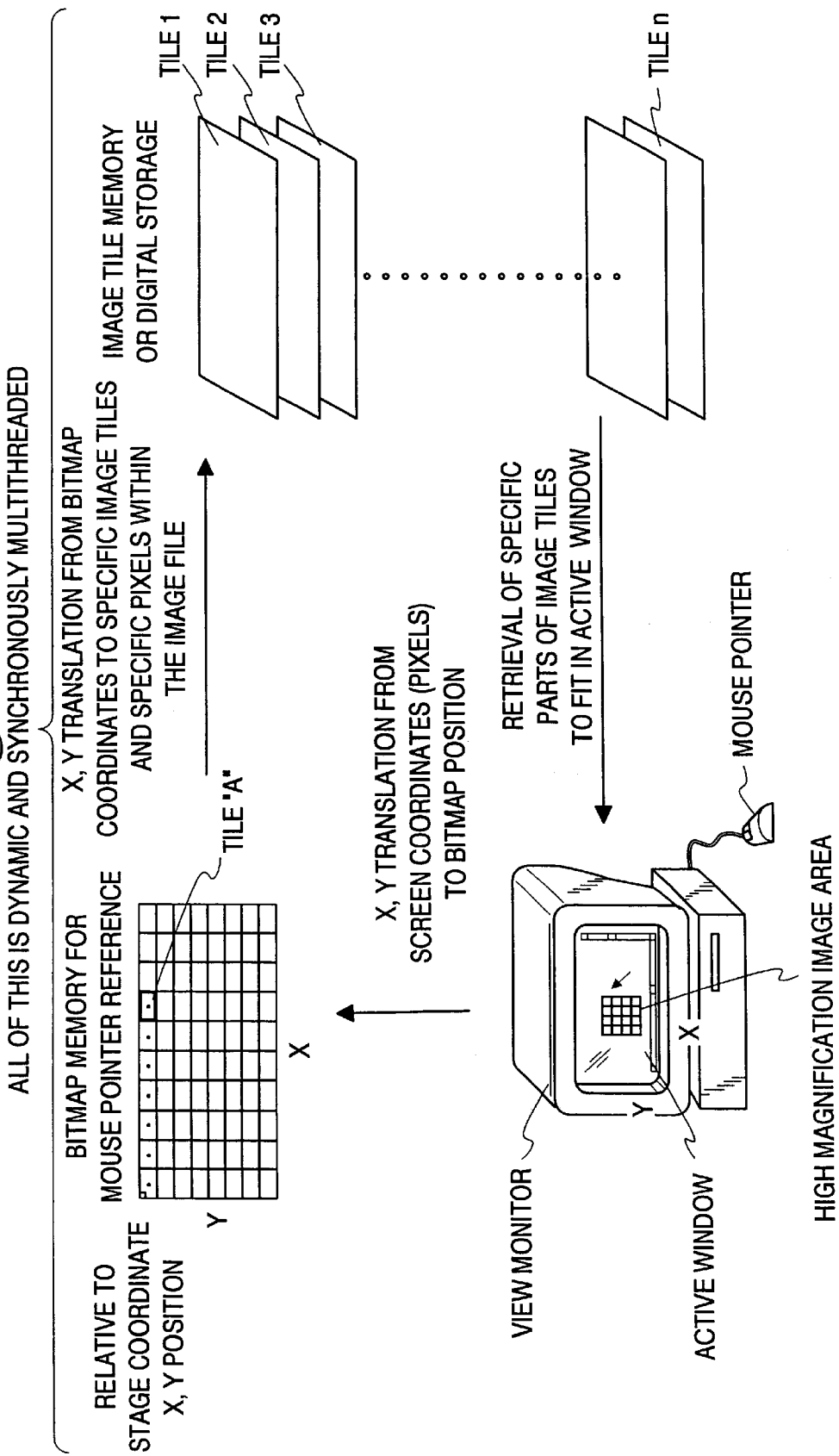
FIG. 6 is a block diagram of the steps in the mapping of the scanned image from the optical sensor array to computer bit map in memory to the display on a user's monitor.

FIG. 6 is a block diagram showing how the control program locates and scrolls through the stored image tiles. Using the example from FIG. 1a, a complete data structure has been created. When the user loads the data structure (of the microscope slide) into his personal computer or views it from an Internet browser, the control program recreates a bit map of the stored data. The bit map of the entire slide is shown in FIG. 6. Image tile A is also high-lighted. This bit map enables a user to point to or otherwise reference a location on the slide.

The X-Y coordinate information specified in the data structure enables X-Y translation of the specific image tiles and specific pixels within the image tile. When the control program first loads the image, because this image file is so large, only a small number of the available tiles are displayed in the active window on the user's monitor. The user uses his mouse or pointing device to scroll through the active window to view the entire macro image. The X-Y coordinate information selected by the mouse translates into specific image tiles or portions therein. The computer takes the mouse pointer information and retrieves the image data from the series of stored tile images and displays them on the monitor for viewing the by user.

Because of the large amount of CCD pixel information stored, actual CCD pixel information can be recreated in the viewing window. The entire system operates in a loop, where the user inputs a mouse location, the computer translates the mouse location from the screen coordinates (screen pixels) to the X-Y coordinates on the bit map.

Similarly, the user may select the high magnification data images. These are outlined by a dark grid, indicating the areas stored. The user operates the mouse in the same manner as described above. The control program locates the stored X-Y coordinates and retrieves the selected parts of the image, CCD stored pixel by CCD stored pixel.

As mentioned above, to save storage space, computer 32 can perform a data compression on each of the image tile files. A preferred data compression is JPEG, which is readily transferred and recognized by most Internet browser programs. Also, JPEG allows flexibility in the amount of data to be compressed, from 20 to 80 percent. FIG. 8 is file listing such as would be seen under Windows 95 file manager showing the data files included in an alternate data structure, one in which the data files have been compressed or converted to JPEG (.jpg) format for a breast cancer specimen. The file index.html (shown in Table 3) is the listing which contains the X-Y coordinate information for these data files. This is the information that is read by the dynamic, self-executing program for viewing, reconstructing and manipulating the image tiles into the macro and micro views.

TABLE 3 index.html

<HTML>
<TITLE>
DCIS_027 - Web Slide
</TITLE>
<BODY>
<APPLET CODE=WebSlide/BliWebSlide.class NAME=DCIS_027
WIDTH=3384 HEIGHT=960 HSPACE=0 VSPACE=0 ALIGN=Middle>
<PARAM NAME = "tPatientID" VALUE = "mda027">

TABLE 3-continued index.html

```
<PARAM NAME = "tAccession" VALUE = " ">
<PARAM NAME = "tOperatorID" VALUE = "jwb">
<PARAM NAME = "tTimeOfScan" VALUE = "8/4/97 1:19:56 PM">
<PARAM NAME = "lXStageRef" VALUE = "278000">
<PARAM NAME = "lYStageRef" VALUE = "142500">
<PARAM NAME = "iImageWidth" VALUE = "752">
<PARAM NAME = "iImageHeight" VALUE = "480">
<PARAM NAME = "lXStepSize" VALUE = "1590">
<PARAM NAME = "lYStepSize" VALUE = "1190">
<PARAM NAME = "lXOffset" VALUE = "-1900">
<PARAM NAME = "lYOffset" VALUE = "-400">
<PARAM NAME = "dMagnification" VALUE = "40">
<PARAM NAME = "iImageCount" VALUE = "105">
<PARAM NAME = "lXSsStepSize" VALUE = "48143">
<PARAM NAME = "lYSsStepSize" VALUE = "35800">
<PARAM NAME = "iScannedCount" VALUE = "37">
<PARAM NAME = "lStartX" VALUE = "278000">
<PARAM NAME = "lStartY" VALUE = "142500">
<PARAM NAME = "Ss1_X" VALUE = "181714">
<PARAM NAME = "Ss1_Y" VALUE = "142500">
<PARAM NAME = "Ss2_X" VALUE = "133571">
<PARAM NAME = "Ss2_Y" VALUE = "142500">
<PARAM NAME = "Ss3_X" VALUE = "37285">
<PARAM NAME = "Ss3_Y" VALUE = "106700">
<PARAM NAME = "Ss4_X" VALUE = "85428">
<PARAM NAME = "Ss4_Y" VALUE = "106700">
<PARAM NAME = "Ss5_X" VALUE = "133571">
<PARAM NAME = "Ss5_Y" VALUE = "106700">
<PARAM NAME = "Ss6_X" VALUE = "181714">
<PARAM NAME = "Ss6_Y" VALUE = "106700">
<PARAM NAME = "Ss7_X" VALUE = "229857">
<PARAM NAME = "Ss7_Y" VALUE = "106700">
<PARAM NAME = "Ss8_X" VALUE = "229857">
<PARAM NAME = "Ss8_Y" VALUE = "70900">
<PARAM NAME = "Ss9_X" VALUE = "181714">
<PARAM NAME = "Ss9_Y" VALUE = "70900">
<PARAM NAME = "Ss10_X" VALUE = "133571">
<PARAM NAME = "Ss10_Y" VALUE = "70900">
<PARAM NAME = "Ss11_X" VALUE = "85428">
<PARAM NAME = "Ss11_Y" VALUE = "70900">
<PARAM NAME = "Ss12_X" VALUE = "37285">
<PARAM NAME = "Ss12_Y" VALUE = "70900">
<PARAM NAME = "Ss13_X" VALUE = "-10858">
<PARAM NAME = "Ss13_Y" VALUE = "70900">
<PARAM NAME = "Ss14_X" VALUE = "-10858">
<PARAM NAME = "Ss14_Y" VALUE = "35100">
<PARAM NAME = "Ss15_X" VALUE = "37285">
<PARAM NAME = "Ss15_Y" VALUE = "35100">
<PARAM NAME = "Ss16_X" VALUE = "85428">
<PARAM NAME = "Ss16_Y" VALUE = "35100">
<PARAM NAME = "Ss17_X" VALUE = "133571">
<PARAM NAME = "Ss17_Y" VALUE = "35100">
<PARAM NAME = "Ss18_X" VALUE = "181714">
<PARAM NAME = "Ss18_Y" VALUE = "35100">
<PARAM NAME = "Ss19_X" VALUE = "229857">
<PARAM NAME = "Ss19_Y" VALUE = "35100">
<PARAM NAME = "Ss20_X" VALUE = "278000">
<PARAM NAME = "Ss20_Y" VALUE = "-700">
<PARAM NAME = "Ss21_X" VALUE = "229857">
<PARAM NAME = "Ss21_Y" VALUE = "-700">
<PARAM NAME = "Ss22_X" VALUE = "181714">
<PARAM NAME = "Ss22_Y" VALUE = "-700">
<PARAM NAME = "Ss23_X" VALUE = "133571">
<PARAM NAME = "Ss23_Y" VALUE = "-700">
<PARAM NAME = "Ss24_X" VALUE = "85428">
<PARAM NAME = "Ss24_Y" VALUE = "-700">
<PARAM NAME = "Ss25_X" VALUE = "37285">
<PARAM NAME = "Ss25_Y" VALUE = "-700">
<PARAM NAME = "Ss26_X" VALUE = "-10858">
<PARAM NAME = "Ss26_Y" VALUE = "-700">
<PARAM NAME = "Ss27_X" VALUE = "-10858">
<PARAM NAME = "Ss27_Y" VALUE = "-36500">
<PARAM NAME = "Ss28_X" VALUE = "37285">
<PARAM NAME = "Ss28_Y" VALUE = "-36500">
<PARAM NAME = "Ss29_X" VALUE = "85428">
<PARAM NAME = "Ss29_Y" VALUE = "-36500">
<PARAM NAME = "Ss30_X" VALUE = "133571">
<PARAM NAME = "Ss30_Y" VALUE = "-36500">
<PARAM NAME = "Ss31_X" VALUE = "181714">
<PARAM NAME = "Ss31_Y" VALUE = "-36500">
<PARAM NAME = "Ss32_X" VALUE = "229857">
<PARAM NAME = "Ss32_Y" VALUE = "-36500">
<PARAM NAME = "Ss33_X" VALUE = "278000">
<PARAM NAME = "Ss33_Y" VALUE = "-36500">
<PARAM NAME = "Ss34_X" VALUE = "278000">
<PARAM NAME = "Ss34_Y" VALUE = "-72300">
<PARAM NAME = "Ss35_X" VALUE = "229857">
<PARAM NAME = "Ss35_Y" VALUE = "-72300">
<PARAM NAME = "Ss36_X" VALUE = "181714">
<PARAM NAME = "Ss36_Y" VALUE = "-72300">
<PARAM NAME = "Ss37_X" VALUE = "133571">
<PARAM NAME = "Ss37_Y" VALUE = "-72300">
<PARAM NAME = "Da0_X" VALUE = "214532">
<PARAM NAME = "Da0_Y" VALUE = "65584">
<PARAM NAME = "Da1_X" VALUE = "212996">
<PARAM NAME = "Da1_Y" VALUE = "65584">
<PARAM NAME = "Da2_X" VALUE = "211460">
<PARAM NAME = "Da2_Y" VALUE = "65584">
<PARAM NAME = "Da3_X" VALUE = "209924">
<PARAM NAME = "Da3_Y" VALUE = "65584">
<PARAM NAME = "Da4_X" VALUE = "208388">
<PARAM NAME = "Da4_Y" VALUE = "65584">
<PARAM NAME = "Da5_X" VALUE = "206852">
<PARAM NAME = "Da5_Y" VALUE = "65584">
<PARAM NAME = "Da6_X" VALUE = "205316">
<PARAM NAME = "Da6_Y" VALUE = "65584">
<PARAM NAME = "Da7_X" VALUE = "203780">
<PARAM NAME = "Da7_Y" VALUE = "65584">
<PARAM NAME = "Da8_X" VALUE = "214532">
<PARAM NAME = "Da8_Y" VALUE = "64400">
<PARAM NAME = "Da9_X" VALUE = "212996">
<PARAM NAME = "Da9_Y" VALUE = "64400">
<PARAM NAME = "Da10_X" VALUE = "211460">
<PARAM NAME = "Da10_Y" VALUE = "64400">
<PARAM NAME = "Da11_X" VALUE = "209924">
<PARAM NAME = "Da11_Y" VALUE = "64400">
<PARAM NAME = "Da12_X" VALUE = "208388">
<PARAM NAME = "Da12_Y" VALUE = "64400">
<PARAM NAME = "Da13_X" VALUE = "206852">
<PARAM NAME = "Da13_Y" VALUE = "64400">
<PARAM NAME = "Da14_X" VALUE = "205316">
<PARAM NAME = "Da14_Y" VALUE = "64400">
<PARAM NAME = "Da15_X" VALUE = "203780">
<PARAM NAME = "Da15_Y" VALUE = "64400">
<PARAM NAME = "Da16_X" VALUE = "214532">
<PARAM NAME = "Da16_Y" VALUE = "63216">
<PARAM NAME = "Da17_X" VALUE = "212996">
<PARAM NAME = "Da17_Y" VALUE = "63216">
<PARAM NAME = "Da18_X" VALUE = "211460">
<PARAM NAME = "Da18_Y" VALUE = "63216">
<PARAM NAME = "Da19_X" VALUE = "209924">
<PARAM NAME = "Da19_Y" VALUE = "63216">
<PARAM NAME = "Da20_X" VALUE = "208388">
<PARAM NAME = "Da20_Y" VALUE = "63216">
<PARAM NAME = "Da21_X" VALUE = "206852">
<PARAM NAME = "Da21_Y" VALUE = "63216">
<PARAM NAME = "Da22_X" VALUE = "205316">
<PARAM NAME = "Da22_Y" VALUE = "63216">
<PARAM NAME = "Da23_X" VALUE = "203780">
<PARAM NAME = "Da23_Y" VALUE = "63216">
<PARAM NAME = "Da24_X" VALUE = "214532">
<PARAM NAME = "Da24_Y" VALUE = "62032">
<PARAM NAME = "Da25_X" VALUE = "212996">
<PARAM NAME = "Da25_Y" VALUE = "62032">
<PARAM NAME = "Da26_X" VALUE = "211460">
<PARAM NAME = "Da26_Y" VALUE = "62032">
<PARAM NAME = "Da27_X" VALUE = "209924">
<PARAM NAME = "Da27_Y" VALUE = "62032">
<PARAM NAME = "Da28_X" VALUE = "208388">
<PARAM NAME = "Da28_Y" VALUE = "62032">
<PARAM NAME = "Da29_X" VALUE = "206852">
<PARAM NAME = "Da29_Y" VALUE = "62032">
<PARAM NAME = "Da30_X" VALUE = "205316">
<PARAM NAME = "Da30_Y" VALUE = "62032">
```

TABLE 3-continued index.html

```
<PARAM NAME = "Da31_X" VALUE = "203780">
<PARAM NAME = "Da31_Y" VALUE = "62032">
<PARAM NAME = "Da32_X" VALUE = "214532">
<PARAM NAME = "Da32_Y" VALUE = "60848">
<PARAM NAME = "Da33_X" VALUE = "212996">
<PARAM NAME = "Da33_Y" VALUE = "60848">
<PARAM NAME = "Da34_X" VALUE = "211460">
<PARAM NAME = "Da34_Y" VALUE = "60848">
<PARAM NAME = "Da35_X" VALUE = "209924">
<PARAM NAME = "Da35_Y" VALUE = "60848">
<PARAM NAME = "Da36_X" VALUE = "208388">
<PARAM NAME = "Da36_Y" VALUE = "60848">
<PARAM NAME = "Da37_X" VALUE = "206852">
<PARAM NAME = "Da37_Y" VALUE = "60848">
<PARAM NAME = "Da38_X" VALUE = "205316">
<PARAM NAME = "Da38_Y" VALUE = "60848">
<PARAM NAME = "Da39_X" VALUE = "203780">
<PARAM NAME = "Da39_Y" VALUE = "60848">
<PARAM NAME = "Da40_X" VALUE = "214532">
<PARAM NAME = "Da40_Y" VALUE = "59664">
<PARAM NAME = "Da41_X" VALUE = "212996">
<PARAM NAME = "Da41_Y" VALUE = "59664">
<PARAM NAME = "Da42_X" VALUE = "211460">
<PARAM NAME = "Da42_Y" VALUE = "59664">
<PARAM NAME = "Da43_X" VALUE = "209924">
<PARAM NAME = "Da43_Y" VALUE = "59664">
<PARAM NAME = "Da44_X" VALUE = "208388">
<PARAM NAME = "Da44_Y" VALUE = "59664">
<PARAM NAME = "Da45_X" VALUE = "206852">
<PARAM NAME = "Da45_Y" VALUE = "59664">
<PARAM NAME = "Da46_X" VALUE = "205316">
<PARAM NAME = "Da46_Y" VALUE = "59664">
<PARAM NAME = "Da47_X" VALUE = "203780">
<PARAM NAME = "Da47_Y" VALUE = "59664">
<PARAM NAME = "Da48_X" VALUE = "214532">
<PARAM NAME = "Da48_Y" VALUE = "58480">
<PARAM NAME = "Da49_X" VALUE = "212996">
<PARAM NAME = "Da49_Y" VALUE = "58480">
<PARAM NAME = "Da50_X" VALUE = "211460">
<PARAM NAME = "Da50_Y" VALUE = "58480">
<PARAM NAME = "Da51_X" VALUE = "209924">
<PARAM NAME = "Da51_Y" VALUE = "58480">
<PARAM NAME = "Da52_X" VALUE = "208388">
<PARAM NAME = "Da52_Y" VALUE = "58480">
<PARAM NAME = "Da53_X" VALUE = "206852">
<PARAM NAME = "Da53_Y" VALUE = "58480">
<PARAM NAME = "Da54_X" VALUE = "205316">
<PARAM NAME = "Da54_Y" VALUE = "58480">
<PARAM NAME = "Da55_X" VALUE = "203780">
<PARAM NAME = "Da55_Y" VALUE = "58480">
<PARAM NAME = "Da56_X" VALUE = "180740">
<PARAM NAME = "Da56_Y" VALUE = "82160">
<PARAM NAME = "Da57_X" VALUE = "179204">
<PARAM NAME = "Da57_Y" VALUE = "82160">
<PARAM NAME = "Da58_X" VALUE = "177668">
<PARAM NAME = "Da58_Y" VALUE = "82160">
<PARAM NAME = "Da59_X" VALUE = "176132">
<PARAM NAME = "Da59_Y" VALUE = "82160">
<PARAM NAME = "Da60_X" VALUE = "174596">
<PARAM NAME = "Da60_Y" VALUE = "82160">
<PARAM NAME = "Da61_X" VALUE = "173060">
<PARAM NAME = "Da61_Y" VALUE = "82160">
<PARAM NAME = "Da62_X" VALUE = "171524">
<PARAM NAME = "Da62_Y" VALUE = "82160">
<PARAM NAME = "Da63_X" VALUE = "180740">
<PARAM NAME = "Da63_Y" VALUE = "80976">
<PARAM NAME = "Da64_X" VALUE = "179204">
<PARAM NAME = "Da64_Y" VALUE = "80976">
<PARAM NAME = "Da65_X" VALUE = "177668">
<PARAM NAME = "Da65_Y" VALUE = "80976">
<PARAM NAME = "Da66_X" VALUE = "176132">
<PARAM NAME = "Da66_Y" VALUE = "80976">
<PARAM NAME = "Da67_X" VALUE = "174596">
<PARAM NAME = "Da67_Y" VALUE = "80976">
<PARAM NAME = "Da68_X" VALUE = "173060">
<PARAM NAME = "Da68_Y" VALUE = "80976">
<PARAM NAME = "Da69_X" VALUE = "171524">
<PARAM NAME = "Da69_Y" VALUE = "80976">
<PARAM NAME = "Da70_X" VALUE = "180740">
<PARAM NAME = "Da70_Y" VALUE = "79792">
<PARAM NAME = "Da71_X" VALUE = "179204">
<PARAM NAME = "Da71_Y" VALUE = "79792">
<PARAM NAME = "Da72_X" VALUE = "177668">
<PARAM NAME = "Da72_Y" VALUE = "79792">
<PARAM NAME = "Da73_X" VALUE = "176132">
<PARAM NAME = "Da73_Y" VALUE = "79792">
<PARAM NAME = "Da74_X" VALUE = "174596">
<PARAM NAME = "Da74_Y" VALUE = "79792">
<PARAM NAME = "Da75_X" VALUE = "173060">
<PARAM NAME = "Da75_Y" VALUE = "79792">
<PARAM NAME = "Da76_X" VALUE = "171524">
<PARAM NAME = "Da76_Y" VALUE = "79792">
<PARAM NAME = "Da77_X" VALUE = "180740">
<PARAM NAME = "Da77_Y" VALUE = "78608">
<PARAM NAME = "Da78_X" VALUE = "179204">
<PARAM NAME = "Da78_Y" VALUE = "78608">
<PARAM NAME = "Da79_X" VALUE = "177668">
<PARAM NAME = "Da79_Y" VALUE = "78608">
<PARAM NAME = "Da80_X" VALUE = "176132">
<PARAM NAME = "Da80_Y" VALUE = "78608">
<PARAM NAME = "Da81_X" VALUE = "174596">
<PARAM NAME = "Da81_Y" VALUE = "78608">
<PARAM NAME = "Da82_X" VALUE = "173060">
<PARAM NAME = "Da82_Y" VALUE = "78608">
<PARAM NAME = "Da83_X" VALUE = "171524">
<PARAM NAME = "Da83_Y" VALUE = "78608">
<PARAM NAME = "Da84_X" VALUE = "180740">
<PARAM NAME = "Da84_Y" VALUE = "77424">
<PARAM NAME = "Da85_X" VALUE = "179204">
<PARAM NAME = "Da85_Y" VALUE = "77424">
<PARAM NAME = "Da86_X" VALUE = "177668">
<PARAM NAME = "Da86_Y" VALUE = "77424">
<PARAM NAME = "Da87_X" VALUE = "176132">
<PARAM NAME = "Da87_Y" VALUE = "77424">
<PARAM NAME = "Da88_X" VALUE = "174596">
<PARAM NAME = "Da88_Y" VALUE = "77424">
<PARAM NAME = "Da89_X" VALUE = "173060">
<PARAM NAME = "Da89_Y" VALUE = "77424">
<PARAM NAME = "Da90_X" VALUE = "171524">
<PARAM NAME = "Da90_Y" VALUE = "77424">
<PARAM NAME = "Da91_X" VALUE = "180740">
<PARAM NAME = "Da91_Y" VALUE = "76240">
<PARAM NAME = "Da92_X" VALUE = "179204">
<PARAM NAME = "Da92_Y" VALUE = "76240">
<PARAM NAME = "Da93_X" VALUE = "177668">
<PARAM NAME = "Da93_Y" VALUE = "76240">
<PARAM NAME = "Da94_X" VALUE = "176132">
<PARAM NAME = "Da94_Y" VALUE = "76240">
<PARAM NAME = "Da95_X" VALUE = "174596">
<PARAM NAME = "Da95_Y" VALUE = "76240">
<PARAM NAME = "Da96_X" VALUE = "173060">
<PARAM NAME = "Da96_Y" VALUE = "76240">
<PARAM NAME = "Da97_X" VALUE = "171524">
<PARAM NAME = "Da97_Y" VALUE = "76240">
<PARAM NAME = "Da98_X" VALUE = "180740">
<PARAM NAME = "Da98_Y" VALUE = "75056">
<PARAM NAME = "Da99_X" VALUE = "179204">
<PARAM NAME = "Da99_Y" VALUE = "75056">
<PARAM NAME = "Da100_X" VALUE = "177668">
<PARAM NAME = "Da100_Y" VALUE = "75056">
<PARAM NAME = "Da101_X" VALUE = "176132">
<PARAM NAME = "Da101_Y" VALUE = "75056">
<PARAM NAME = "Da102_X" VALUE = "174596">
<PARAM NAME = "Da102_Y" VALUE = "75056">
<PARAM NAME = "Da103_X" VALUE = "173060">
<PARAM NAME = "Da103_Y" VALUE = "75056">
<PARAM NAME = "Da104_X" VALUE = "171524">
<PARAM NAME = "Da104_Y" VALUE = "75056">
</APPLET>
</BODY>
</HTML>
```

Figure 9B:
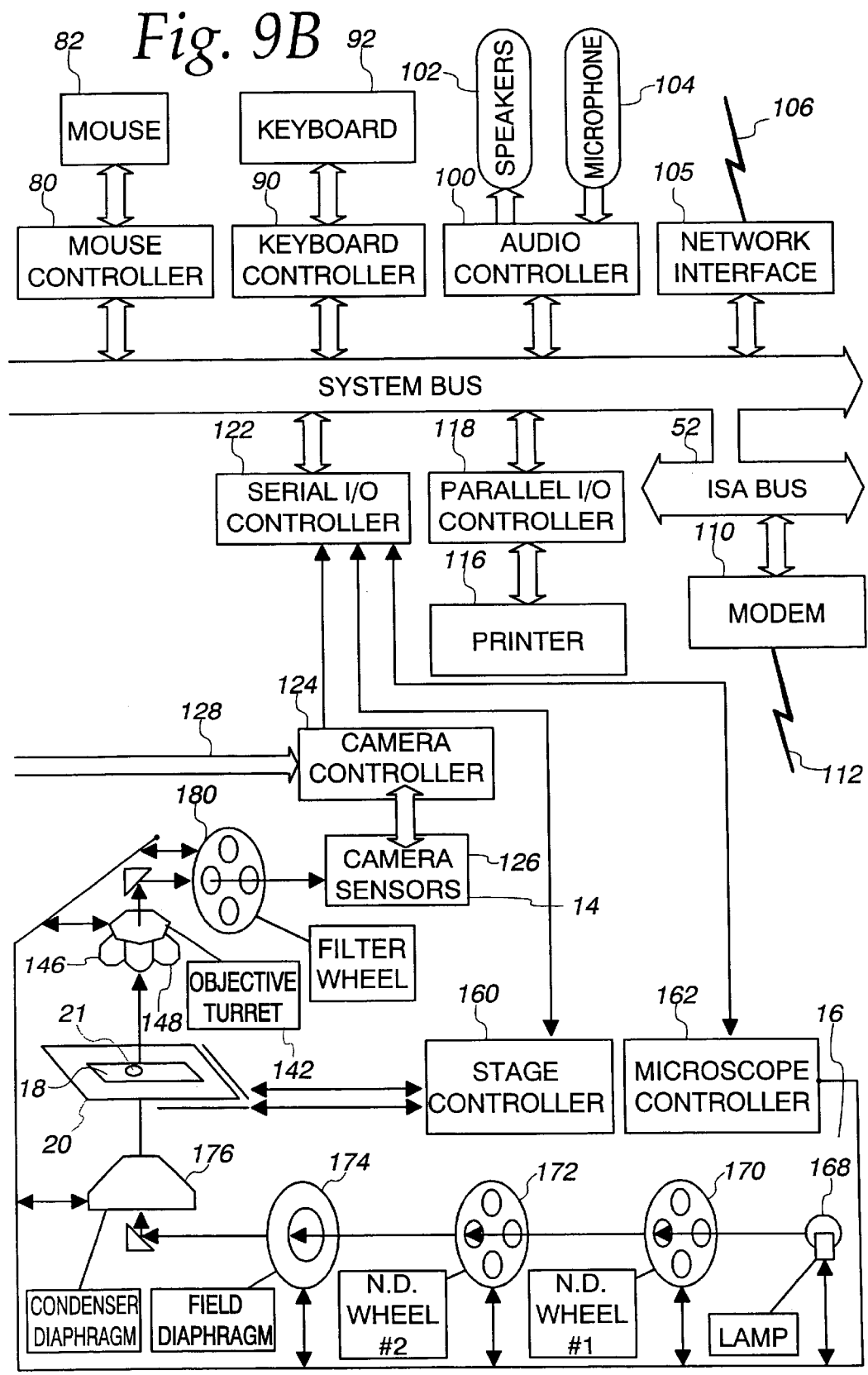
Figure 10:
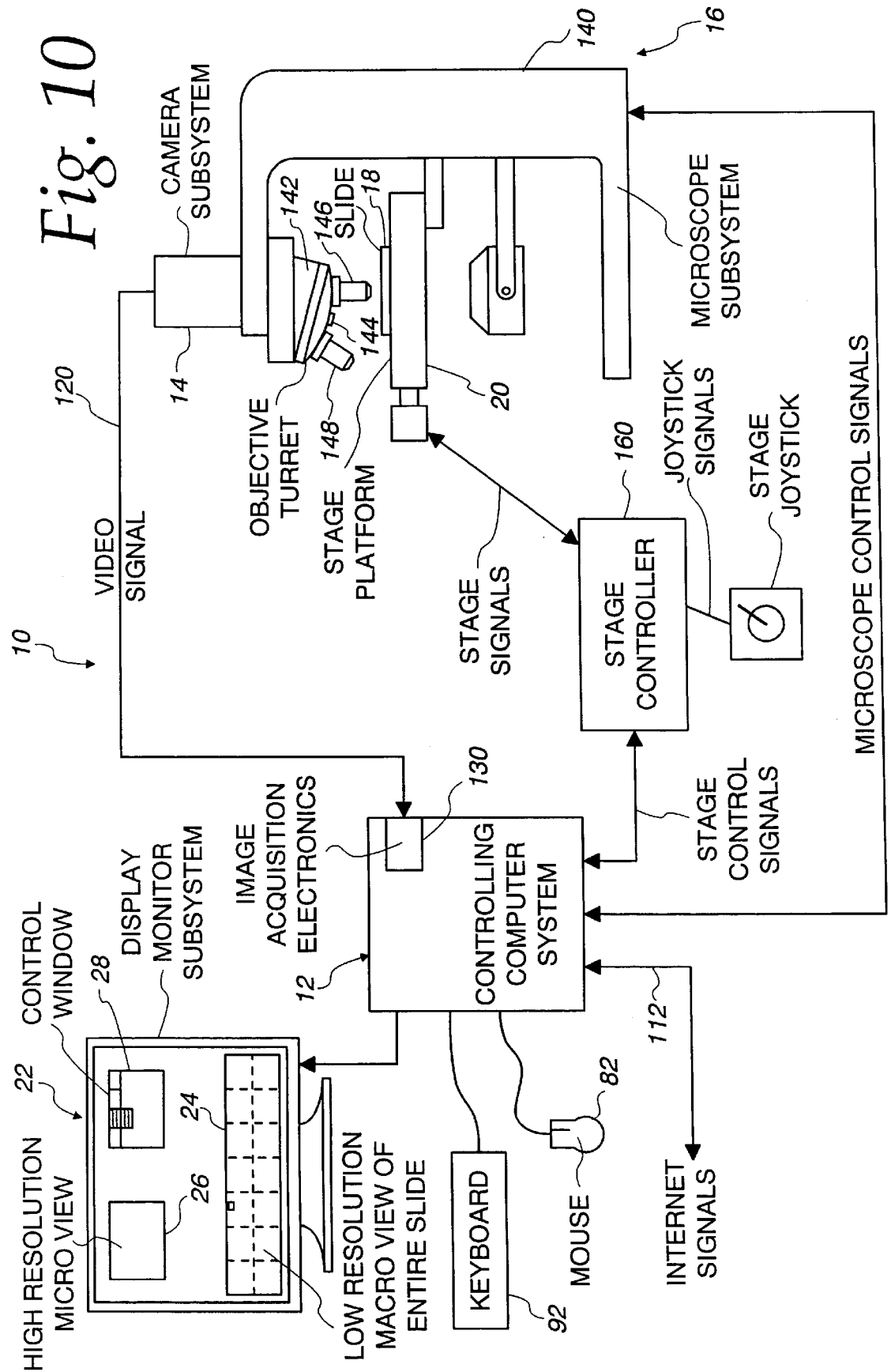
FIG. 10 is a block diagram of a portion of the apparatus shown in FIG. 9 showing details of a mechanical arrangement of a microscope.
Figure 11:
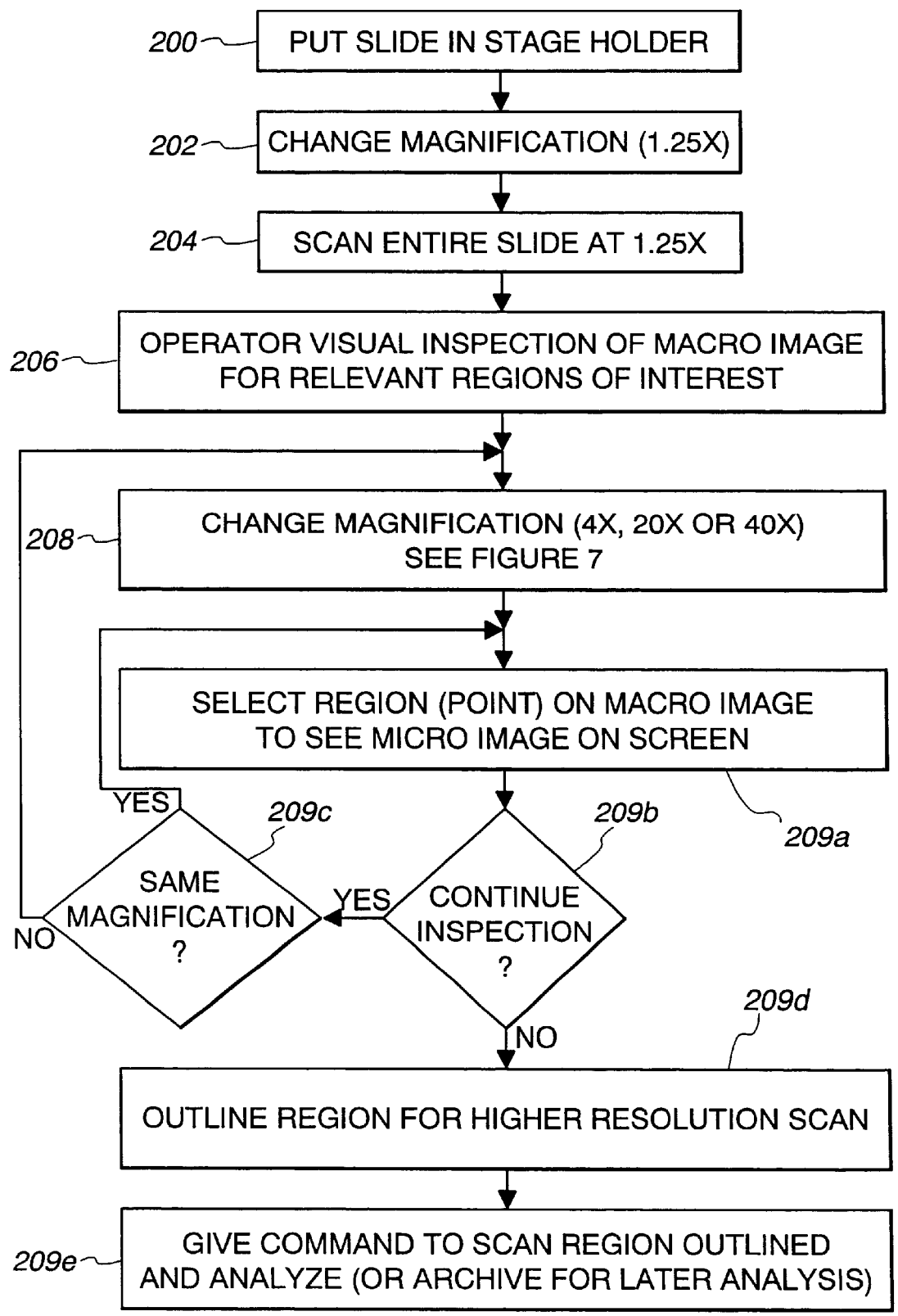
FIG. 11 is a flow diagram related to operation of the apparatus.

Referring now to the drawings, and especially to FIGS. 9A, 9B and 10, apparatus for synthesizing low magnification and high magnification microscopic images is shown therein and generally identified by reference numeral 10. The system includes a computer 12 which is a dual Pentium Pro personal computer in combination with a Hitachi HV-C20 video camera 14 associated with a Zeiss Axioplan 2 microscope 16. The computer system 12 is able to receive signals from the camera 14 which captures light from the microscope 16 having a microscope slide 18 positioned on an LUDL encoded motorized stage 20. The encoded motorized stage 20 includes a MAC 2000 stage controller for controlling the stage in response to the computer 12. A microscope slide 18 includes a biological specimen 21 which is to be viewed by the microscope and whose image is to be digitized both at low magnification and at high magnification as selected by a user. The low magnification digitized image is then displayed on a 21 inch Iiyama video display monitor 22 having resolution of 1600 by 1200 to provide display screens of the type shown in FIGS. 1 through 3 including a low magnification image 24, for instance, at 1.25 power, a high magnification image 26, for instance at 40× power and a control window or image 28. The low magnification image may have identified therein a region 30 which is reproduced at high magnification in high magnification screen or window 26 so that a pathologist or other operator of the system can review architectural regions of interest in low magnification image 24 and simultaneously view them in high magnification in the high magnification screen or window 26 to determine whether the cells forming a portion of the architectural feature need be examined further for cancer or the like or not.

The computer 10 is constructed around a PCI system bus 40 and has a first Pentium Pro microprocessor 42 and a second pentium pro microprocessor 44 connected thereto. The system bus 40 has connected to it a PCI bus 50 and an ISA bus 52. The PCI bus 50 has a SCSI controller 60 connected thereto to send and receive information from a hard disk 62. The hard disk 62 also is coupled in daisy chain SCSI fashion to a high capacity removal disk and to a CD Rom drive 66. The hard disks 62 contains the programs for operating the system for controlling the microscope 16 and for processing the images as well as for doing a quantitative analysis of the selected portions of the histological specimens being viewed on the slide 18. The system bus 40 also has connected to it a random access memory 70 within which portions of the program being executed are stored as well as a read only memory 72 for holding a bootstrap loader as well as portions of the basic input/output operating system. A floppy disk controller 74 is coupled to the system bus 40 and has connected to it a floppy disk drive 76 for reading and writing information to a floppy disk as appropriate. A mouse controller 80 is coupled to the system bus and has a mouse 82 which operates as a pointing device for controlling manipulations on the screen 22 and within the windows 24, 26 and 28. A keyboard controller 90 is connected to the system bus and has a keyboard 92 connected thereto. The keyboard 92 may be used to send and receive alpha numeric signals to other portions of the computer. An audio controller 100 has a plurality of speakers 102 and a microphone 104 connected thereto for audio input and output and is coupled to the system bus 40. A network interface, such as a network interface card 104, is connected to the system bus and can provide signals via a channel 106 to other portions of a network or internet to which the system may be connected. Likewise, signals can be sent out of the system through a modem 110 connected to the ISA bus 52 and may be sent via a channel 112, for instance, to the internet. A printer 116 is connected via a parallel I/O controller 118 to the system bus in order to provide printouts as appropriate of screens and other information as it is generated. A serial I/O controller 122 is connected to the system bus and has connected to it a camera controller 124 which is coupled to CCD sensors 126 in the cameras. The CCD sensors 126 supply pixel or image signals representative of what is found on the slide 18 to an Epix pixci image acquisition controller 130 coupled to the PCI bus 50.

The microscope 16 includes a base 140 having a stage 20 positioned thereon as well as an objective turret 142 having a plurality of objectives 144, 146 and 148 thereon. The objective 144, for instance, may be of 1.25× objective. The objective 146 may be a 20× objective. The objective 148 may be a 40× objective. Signals from the camera sensors and controller are supplied over a bus 128 to the image acquisition system where they are digitized and supplied to the PCI bus for storage in RAM or for backing storage on the hard disk 62.

Figure 14:
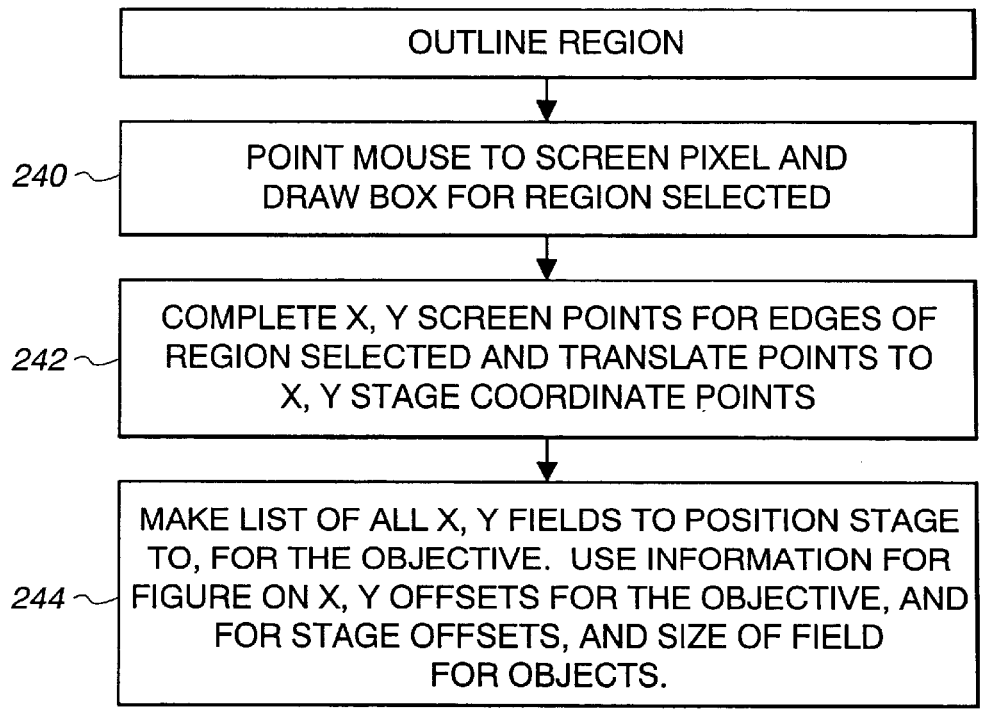
FIG. 14 is a flow chart for a region outlying routine.

When a specimen is on the slide 18 the stage 20 may be manipulated under the control of the computer through a stage controller 160 coupled to the serial I/O controller 122. Likewise, a microscope controller 162 controls aspects of the microscope such as the illumination, the color temperature or spectral output of a lamp 168 and the like. For instance, in normal operation, when a specimen is placed on the slide, specimen slide 18 is placed on the stage 20 in a step 200, as shown in FIG. 14, the processors 42 or 44 send a command through the system bus to cause the serial I/O controller 122 to signal the microscope controller to change magnification to 1.25× in a step 202. This is done by rotating the objective turret of the Axioplan 2 microscope to select the objective 144. Likewise, the controller sets the color temperature of the lamp 168, sets a pair of neutral density filter wheels 170 and 172 and sets a field diaphragm 174 for the correct illumination. A condenser diaphragm 176 is also controlled and a color filter wheel 180 may also be controlled to apply the appropriate filter color to the CCD censors 126 in the camera. The entire slide is then scanned in a step 204. The images are tiled and melded together into the overall image 24 supplied on the screen 22 to provide the operator in the step 206 with a visually inspectable macro image of relevant regions of the slide of interest.

In order to provide the magnified image, the mouse may be moved to identify a marker segment or region which, for instance, may be a rectangular region which will cause the microscope to change magnification as at step 208 to 4×, 20×, 40×, etc., by rotating the turret to bring the appropriate objective lens system into viewing position.

Next the user, in a step 209a, uses the mouse to select the region on the macro image in order to select the micro image to be viewed on the screen 22. In a step 209b a test is made to determine whether the user has commanded continued inspection. If the user has, a test is made in a step 209c to determine if the magnification is to be changed by changing the selected objective. In the event the magnification is to be changed control is transferred to the step 208. If the magnification is to remain unchanged control is transferred to the step 209a. In the event inspection is not to continue the region selected is outlined for higher magnification scan in a step 209d. In a step 209e, a command may be received to scan or acquire the higher magnification image for display in screen 26. The image may then be archived for later analysis, displayed or analyzed immediately.

In order to perform the magnification called for in step 208, the overall illumination and control of the microscope will be controlled so that in a step 210 the objective turret 142 will be rotated to place the higher power objective above the slide 18. In a step 212 voltage to the lamp will be changed to adjust the lamp 168 to provide the proper illumination and color temperature as predetermined for the selected objective. In a step 214, the condenser diaphragm 176 will have its opening selected as appropriate to provide the proper illumination for that objective. In a step 216, the filter turret 180 will select the proper light wavelength filter to be supplied to the camera sensors. For instance, a red, blue or green filter, as appropriate, particularly if the specimen has been stained. In a step 218 the field diaphragm 174 will have its opening changed. In a step 220 the neutral density filter wheel 170 will select a neutral density filter and in a step 222 the neutral density filter wheel 172 will also select a neutral density filter. In a step 224 the X, Y and Z offsets will be used for reconstruction of the recorded image at the magnification and in a step 226 the current position will be read from encoders in the stage which are accurate to 0.10 micron.

In order to identify the selected region the mouse is moved to that area of the region in a pointing operation in a step 240 as shown in FIG. 14. The mouse may be moved to draw a box around the region selected. In a step 242 the X and Y screen points are computed for the edges of the regions selected and the computed image or pixel points are translated to stage coordinate points in order to control the stage of the microscope. In a step 244 a list of all of the X fields for positioning the stage for the objective is stored in random access memory and may be backed up on the hard disk. The information from the X offsets for the objective and the stage offsets is used as well as the size of the field to position the slide properly under the objective to capture the micro image.

Figure 15:
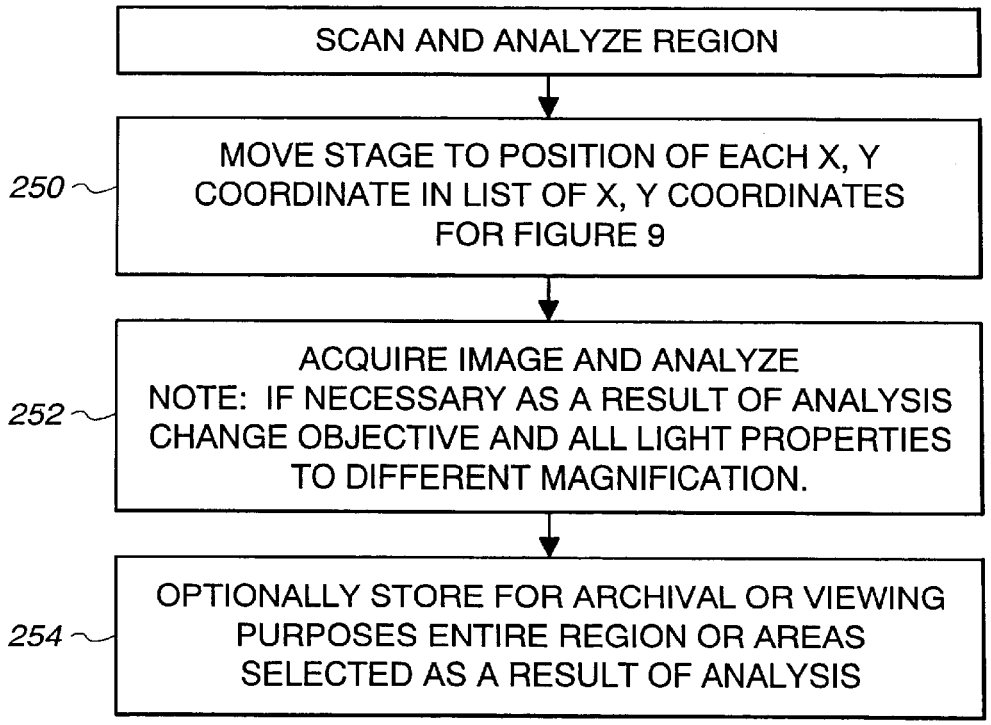
FIG. 15 is a flow chart for a scanning and analyzing routine.

When the slide has been positioned properly, as shown in FIG. 15 in a step 250 the stage is positioned for each of the X and Y coordinate values in stage coordinate values and the digitized image is captured by the cameras and stored in RAM and backed up on the hard disk. The image may be then analyzed quantitatively in various manners such as those set forth in the previously-identified United States application. Optionally the image may be stored for archival purposes in a step 254.

Figure 12:
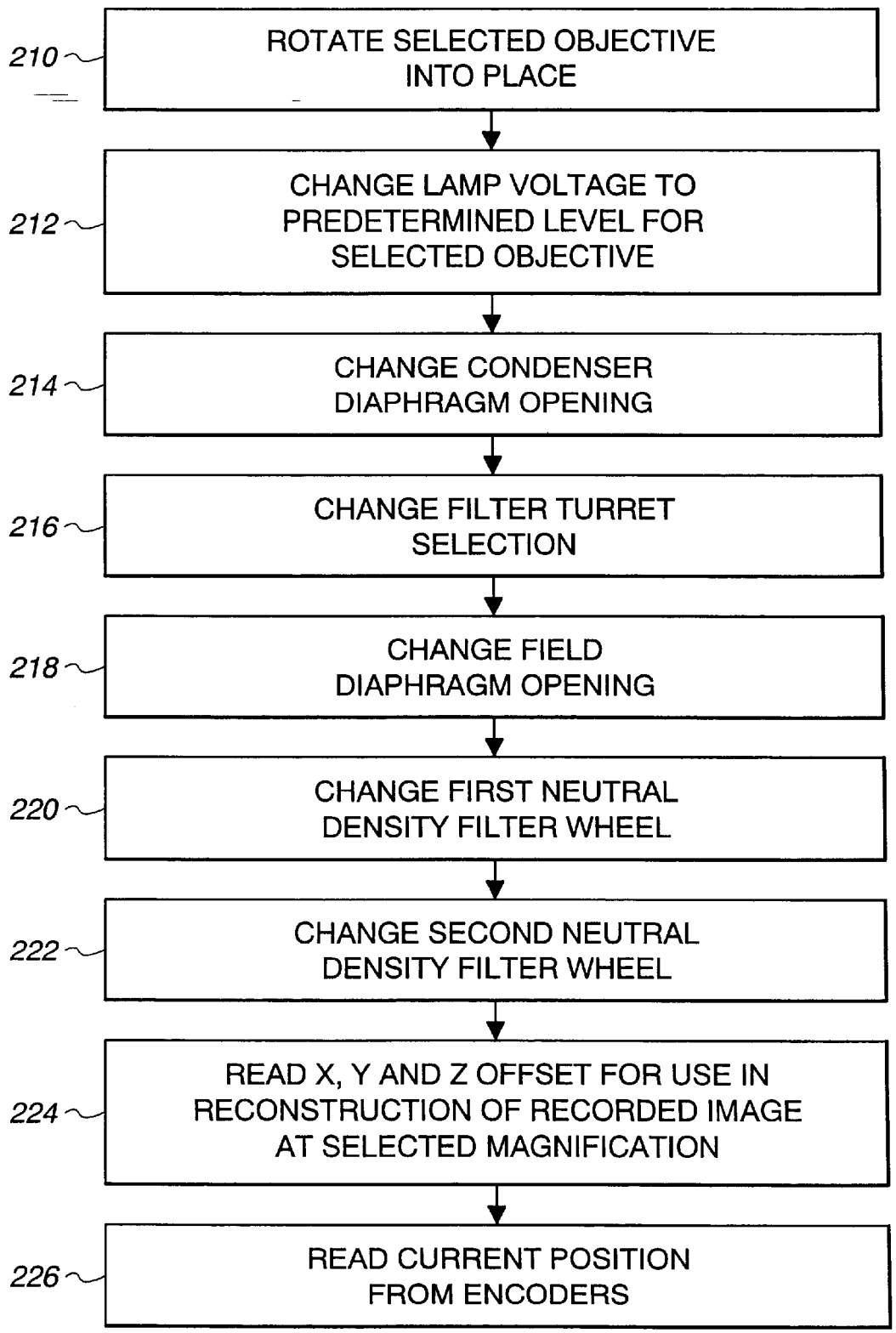
FIG. 12 is a flow diagram of details of one of the steps in FIG. 11.
Figure 13:
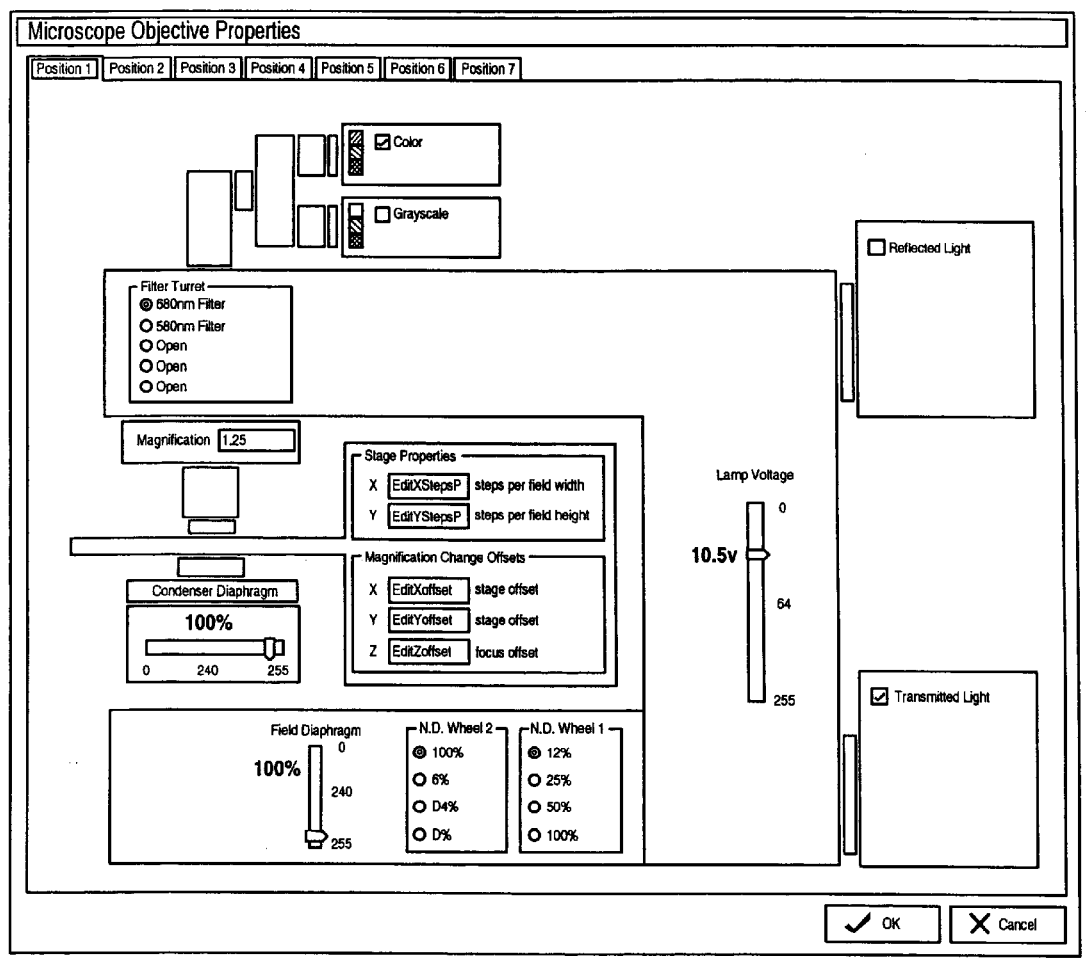
FIG. 13 is a display screen showing control parameters to be manipulated thereon.

In order to override the specific control functions that take place as shown in FIG. 12, a screen is provided as shown in FIG. 13 wherein the X-Y step size can be edited, the X, Y and Z offset can be edited, the lamp voltage can be selected, the neutral density filter can be selected as well as the opening of the field diaphragm and several other microscopic characteristics. FIG. 13 is a view of the settings of the microscope objective properties of the Axioplan 2, computer-controlled microscope.

Figure 16:
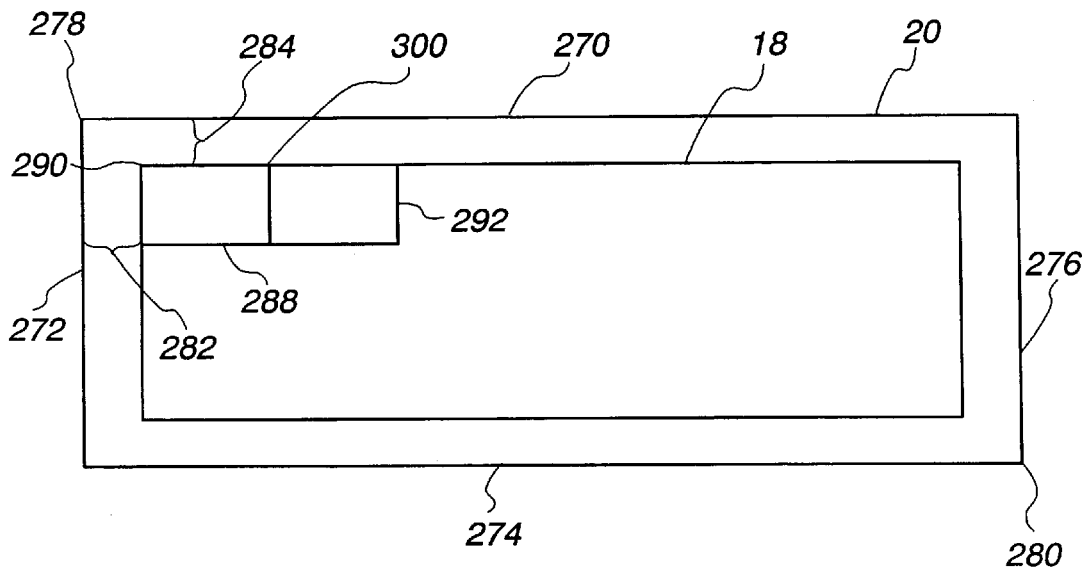
FIG. 16 is a schematic showing of the limits of travel of the microscope stage with respect to the image tiles.

The X and Y positioning is specifically carried out as shown in FIG. 16 where the slide 18 is shown with a slide boundary 270, 272, 274 and 276. Stage boundary for limits of the stage travel for purposes of the stage the stage can be moved all the way from an upper left hand corner of travel 276 to a lower right hand corner of travel 280. At the upper left hand bounded corner of travel 278 limits which a signal that the end of travel has been reached and the stage is then translated a short distance 282 in the extra action and a short distance 284 in the Y direction to define the first tile 288 in terms of a reference point 290 at its upper left hand corner. Since the size of the macro image tile 288 is known, the next macro image tile 292 may be placed contiguous with it by moving the stage appropriately and by measuring the location of the stage from the stage in counters without the necessity of performing any image manipulation. The image tiles 288 and 292 may be abutted without any substantial overlap or they may be overlapped slightly, such as a one pixel with overlap, which is negligible insofar as blurring of any adjacent edges of abutted image tiles. The upper left hand corner 300 of the tile 292 defines the rest of 292 and other tiles can be so defined. Micro image tiles can likewise be defined so that they are contiguous but not substantially overlapping, as would interfere with the composite image. This avoids the problems encountered with having to perform extended computations on digital images in a frame storer or multiple frame storage in order to match or bring the images into contiguity without blurriness at the edges of contiguous image tiles. It may be appreciated that the low power image 24 has a plurality of micro images defined therein which are tiled and which are shown in higher magnification as individual tiles 312, 314, 316 and the like. In addition, the region 310 when magnified as shown in the window 26 may exceed the bounds of the window and thus the window may include scroll bars or other means for allowing the image 310 which is larger than the window 26 to be examined from within the window 26.

Figure 16A:
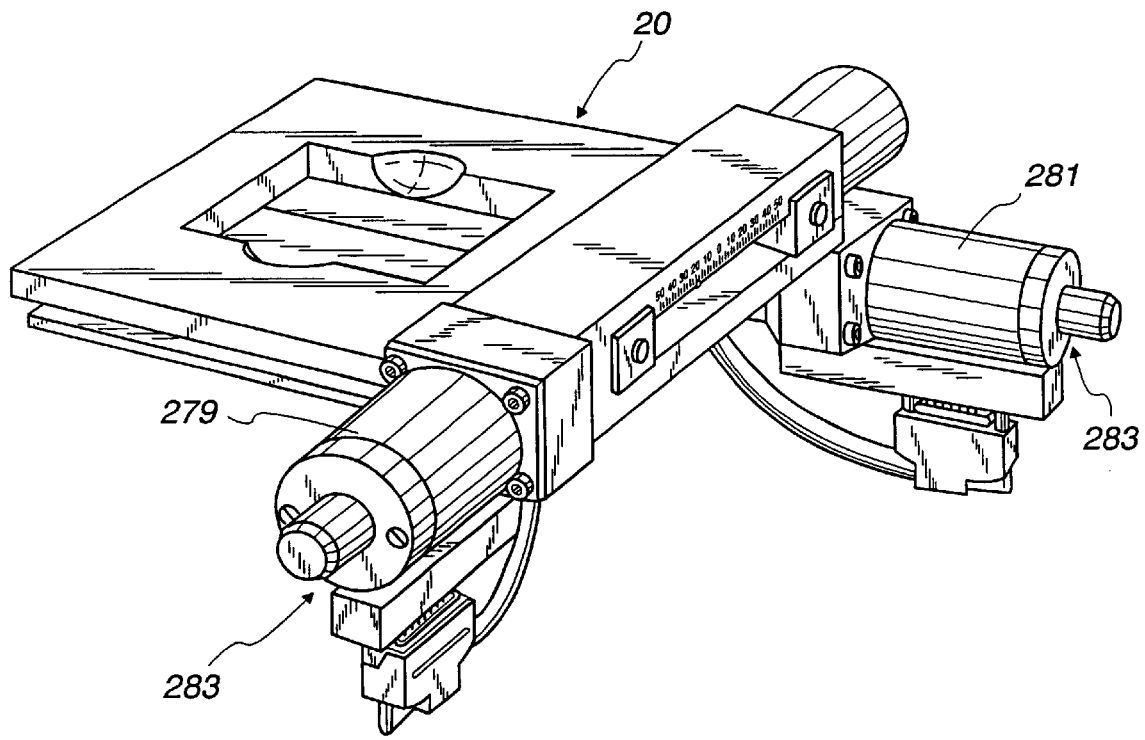
FIG. 16A is a perspective view of the microscope stage and stepper motors and encoders providing a closed loop drive for the motors.
Figure 17:
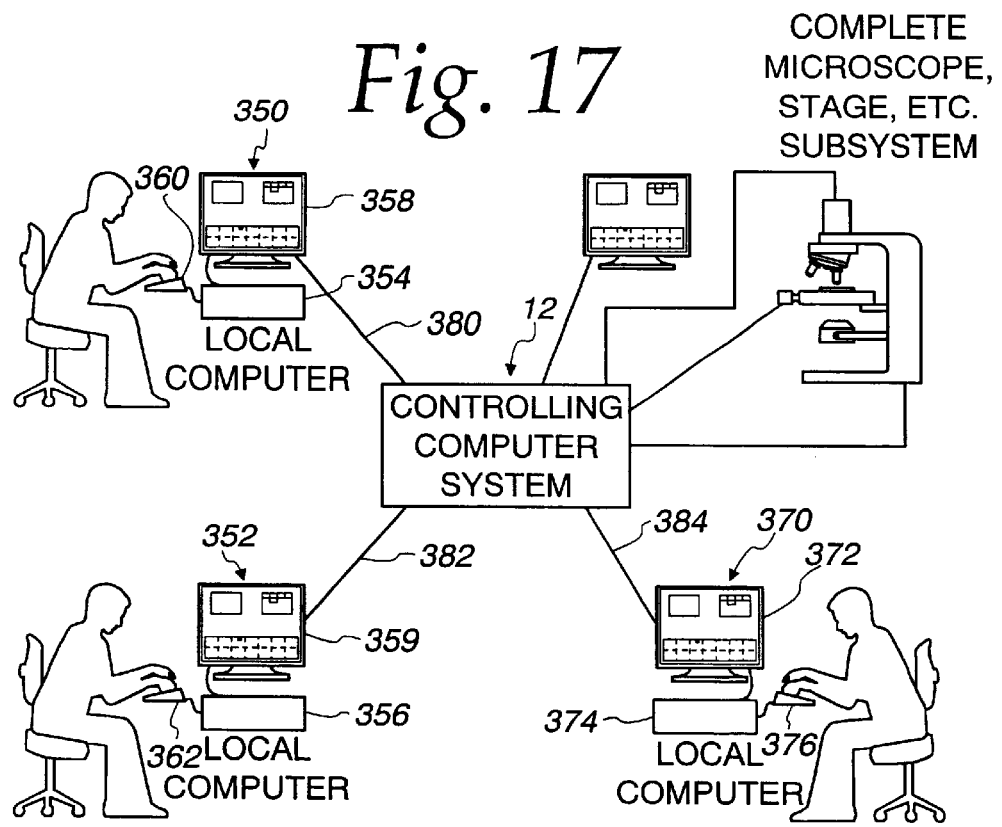
FIG. 17 is a block diagram of a networked system allowing multiple workstations to obtain access to the microscope and to manipulate the microscope locally at each workstation.
Figure 17A:
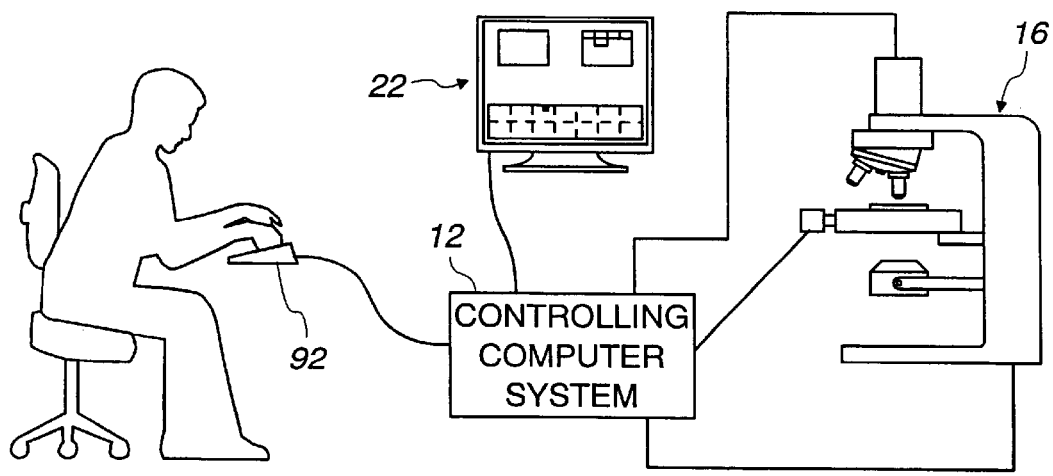
FIG. 17A is a view of the system described in connection with FIG. 10.

The stage 200 is best seen in FIG. 16A and includes the X and Y stepper motors 279 and 281 with their respective encoders, which provide a closed loop system to give the 0.1 micron accuracy versus the usual 5 or 6 micron accuracy of most microscope stages without a closed loop system. This closed loop system and this very high accuracy allow the abutting of the tile images for both high magnification and low magnification images without the substantial overlap and the time-consuming and expensive software currently used to eliminate the overlap and blurriness at the overlapping edges of adjacent image tiles. With the precisely positioned stage and by using the tiling system described in connection with FIG. 16, where the slide is precisely positioned relative to a center point CP for the slide, and the known position of point 278 is always taken from the same point, the tiles may be positioned precisely in a horizontal row and precisely in vertical rows to reconstruct the macro image and the micro image. This reconstruction is done without the use, as in the prior art, of extensive software manipulation to eliminate overlapping image tiles, horizontally or vertically or the haphazard orientation of image tiles.

The present invention also includes the facility for allowing remote observation to occur by being able to couple the system either over a network communication facility to an intranet, for instance via the network interface, or via a modem or other suitable connection, to an internet so that once the image has been scanned and stored in memory on hard disks or other storage, remote users may be able to access the low magnification image as well as the high magnification image and move around within both images to make determinations as to the histological characteristics of the samples.

An additional feature of the system includes a plurality of networked workstations coupled to a first computer console 12 having a display screen 22 connected to the microscope 14. Satellite work stations 350 and 352 are substantially identical to the work station 12 including respective computers 354 and 356 coupled to displays 358 and 360. The devices can be manipulated through input devices 360 and 362 which may include a keyboard, mouse and the like. Also a third device can be connected including a work station 370, having a display 372, a computer 374 and an input device 376. Each of the devices is connected over respective network lines 380, 382, 384 to the computer 12 which transmission may be via either net or the like. Each of the different operators at the physically separate viewing stations can locate regions from the view of entire tissue cross sections via a macro view and label the regions for subsequent scanning and/or quantitative analysis. A single operator at the instrument station 12 can locate regions to view the entire tissue cross section. Those regions can be labeled for subsequent scanning and/or quantitative analysis with subsequent review and physically remote viewing stations, for instance, in an operating room or in individual pathologists' signout areas in order to review analysis results while still maintaining and reviewing the entire macro view of the tissue and/or the individual stored images from which the quantitative results were obtained. The viewing stations 350, 352 and 370 can comprise desk top computers, laptops, etc. There is no need for a microscope at the network stations 3150, 352 and 370.

In a still further alternative embodiment, remote workstations 400, 402, 404, 406 and 408 may be connected through a server 410 which may be supplied via a packet switched network. The server 410 and may be a hypertext transport protocol based server of the type used for the World Wide Web or may be a telnet type server as used previously in internet remote operation applications. The server 410 communicates via a communications channel 414 with a local computer 416 having a display 418 associated therewith, the local computer 416 being connected to the microscope 420. Each of the remote work stations 400, 402, 404, 406 and 408 may perform the same operations as the stations 350, 352 and 370 although they do it from nearby buildings or even from around the world, thus providing additional flexibility for others to make use of the specimen obtained and being viewed under the microscope 420. In addition, stored images may be disseminated through the server 410 to the remote servers 400 through 408 for further analysis and review.

While there has been illustrated and described a particular embodiment of the present invention, it will be appreciated that numerous changes and modifications will occur to those skilled in the art, and it is intended in the appended claims to cover all those changes and modifications which followed in the true spirit and scope of the present invention.

What is claimed is:

1. A method of constructing and using a self-executing data structure of an image of a specimen on a microscope slide comprising:

digitally scanning and storing multiple magnification and multiple resolution images from the specimen on a microscope slide to create a plurality of individual image tiles having multiple magnifications and multiple resolutions;

providing a dynamic, self-executing program on the data structure for viewing, manipulating and reconstructing the image tiles; and transferring the scanned, digital image tiles with the dynamic, self-executing program to allow viewing of a digital image of substantially larger image area than the area of the individually acquired tiles and at multiple resolutions.

2. The method of claim 1 further comprising the steps of:

displaying a first image comprising a portion of the specimen as an overall macro view; and displaying a second image comprising higher resolution view from the specimen on the microscope slide at a higher magnification than the magnification of the overall macro view.

3. The method of claim 2 further comprising:

selecting a point on said overall macro image with a marker; and producing a corresponding higher magnification image at the location of the marker.

4. A method in accordance with claim 3 wherein the step of selecting a point includes:

moving across tile boundaries to a desired point on a selected macro tile image; and executing a command to product the micro image from the selected macro tile image point.

5. The method of claim 1 further comprising displaying the X-Y coordinates of said point.

6. The method of claim 1 wherein said image tiles are stored as bit-mapped files.

7. The method of claim 6 further comprising converting said bit-mapped files to JPEG files.

8. The method of claim 7, comprising scanning and storing said images of said specimen at at least three magnifications.

9. A method in accordance with claim 1 including the step of transferring the digital images to a web browser.

10. A method in accordance with claim 9 including the step of transferring the data structure having the digital image files and the dynamic, self-executing program over an Internet/intranet communication channel.

11. A method in accordance with claim 9 including the step of retoggling between lower magnification images and higher magnification images stored on the web browser.

12. A method in accordance with claim 1 including the step of:

scrolling a portion of an image being viewed in a direction to cause the image being viewed to shift to include, in a new image, a portion of the image from a neighboring tiled image that was not previously viewed in the last image viewed by a user.

13. An apparatus for creating a data structure comprising:

a computer-controlled microscope imaging system for digitally scanning images from a specimen on a microscope support at a plurality of image magnifications;

a program for recording the scanned digital images in a series of contiguous image tiles; and a program for linking the series of contiguous image tiles with a dynamic, self-executing program effective for viewing, manipulating and reconstructing the image tiles.

14. An apparatus is accordance with claim 13 wherein a data compressor compresses the data of the digitally scanned significantly to allow the scanned digitized images to be sent over the Internet.

15. An apparatus in accordance with claim 13 wherein an addressable coordinate system provides addresses so that images can be seamed together and higher magnification images can be easily located with respect to the lower magnification images.

16. An apparatus in accordance with claim 13 wherein a program for scrolling allows the user to scroll a portion of a neighboring image into view.

17. An apparatus in accordance with claim 13 including an address display to display the coordinates to assist multiple viewers to identify the same area for analysis and commentary.

18. An apparatus in accordance with claim 13 further comprising:

a browser for storing the dynamic, self-executing program; and a monitor for viewing the images stored on the monitor and for flipping back and forth between low resolution macro images and high resolution micro images.

19. An apparatus in accordance with claim 18 including a marker program to mark an addressable area on the macro image and to cause the addressed area to appear at a higher resolution, micro image on the monitor.

20. A program for creating a data structure of an image of a specimen on a microscope slide comprising:
- a scanning routine for digitally scanning the image of the specimen on a microscope slide at a plurality of image magnifications;
- a recording routine for recording the scanned digital image in a series of contiguous image tiles; and
- a linking routine for linking the series of contiguous image tiles with a dynamic, self-executing program effective for viewing, manipulating and reconstructing the image tiles.

21. The program of claim 20 further comprising a first display routine for displaying a micro image comprising a portion of the scanned image at a first magnification and a second display routine for displaying a macro second image comprising an overall view from the specimen on the microscope slide.

22. The program of claim 20 further comprising a routine for selecting a point on said macro image and for producing a corresponding micro image at said point.

23. The program of claim 20 further comprising a coordinate display routine for displaying the coordinates of said point to the user.

* * * * *

UNITED STATES PATENT AND TRADEMARK OFFICE
CERTIFICATE OF CORRECTION

PATENT NO. : 6,775,402 B2
DATED : August 10, 2004
INVENTOR(S) : James W. Bacus et al.

It is certified that error appears in the above-identified patent and that said Letters Patent is hereby corrected as shown below:

Column 30,
Line 10, change "product" to -- produce --.
Line 18, change "7" to -- 1 --.
Line 46, after "scanned" insert -- images --.

Signed and Sealed this

Third Day of May, 2005

JON W. DUDAS
*Director of the United States Patent and Trademark Office*